(12) United States Patent
Kawai et al.

(10) Patent No.: US 7,348,751 B2
(45) Date of Patent: Mar. 25, 2008

(54) APPARATUS FOR DECIDING POSITION OF TRACTION

(75) Inventors: Toshimasa Kawai, Yokohama (JP); Masahito Kobayashi, Ibaraki (JP); Shinya Imura, Ibaraki (JP)

(73) Assignee: Olympus Corporation, Tokyo (JP)

( * ) Notice: Subject to any disclaimer, the term of this patent is extended or adjusted under 35 U.S.C. 154(b) by 700 days.

(21) Appl. No.: 10/620,236

(22) Filed: Jul. 15, 2003

(65) Prior Publication Data
US 2004/0138530 A1   Jul. 15, 2004

(30) Foreign Application Priority Data
Jul. 15, 2002   (JP) ............... 2002-205265

(51) Int. Cl.
*G05D 15/00*  (2006.01)
(52) U.S. Cl. ............... 318/646; 318/461; 318/432; 318/727
(58) Field of Classification Search .............. None
See application file for complete search history.

(56) References Cited

U.S. PATENT DOCUMENTS 4,286,585 A  *  9/1981  Ogawa ............... 600/145
4,941,454 A       7/1990  Wood et al.
6,478,743 B1 * 11/2002  Jordfald et al. ........... 600/462
6,551,302 B1 *  4/2003  Rosinko et al. ........... 604/505
2001/0027268 A1 * 10/2001 Kato ........................ 600/152
2002/0165432 A1 * 11/2002 Matsui ...................... 600/145

FOREIGN PATENT DOCUMENTS

| JP | S63-59329 | 11/1988 |
| JP | H6-22904 | 2/1994 |
| JP | 9-10172 | 1/1997 |
| JP | 2000-300511 | 10/2000 |

* cited by examiner

*Primary Examiner*—Lincoln Donovan
*Assistant Examiner*—Erick Glass
(74) *Attorney, Agent, or Firm*—Scully, Scott, Murphy & Presser, P.C.

(57) ABSTRACT

A hauling unit hauls a subject to bend or rotate the subject. A control unit outputs a control signal that corresponds to a target value that is input by an operating unit. The control unit controls a variation amount of the control signal output in a predetermined range including a position of the hauling unit in a state before the hauling unit hauls to be greater than a variation amount of the control signal output outside the predetermined range. A driving unit drives the hauling unit based on the control signal.

13 Claims, 31 Drawing Sheets

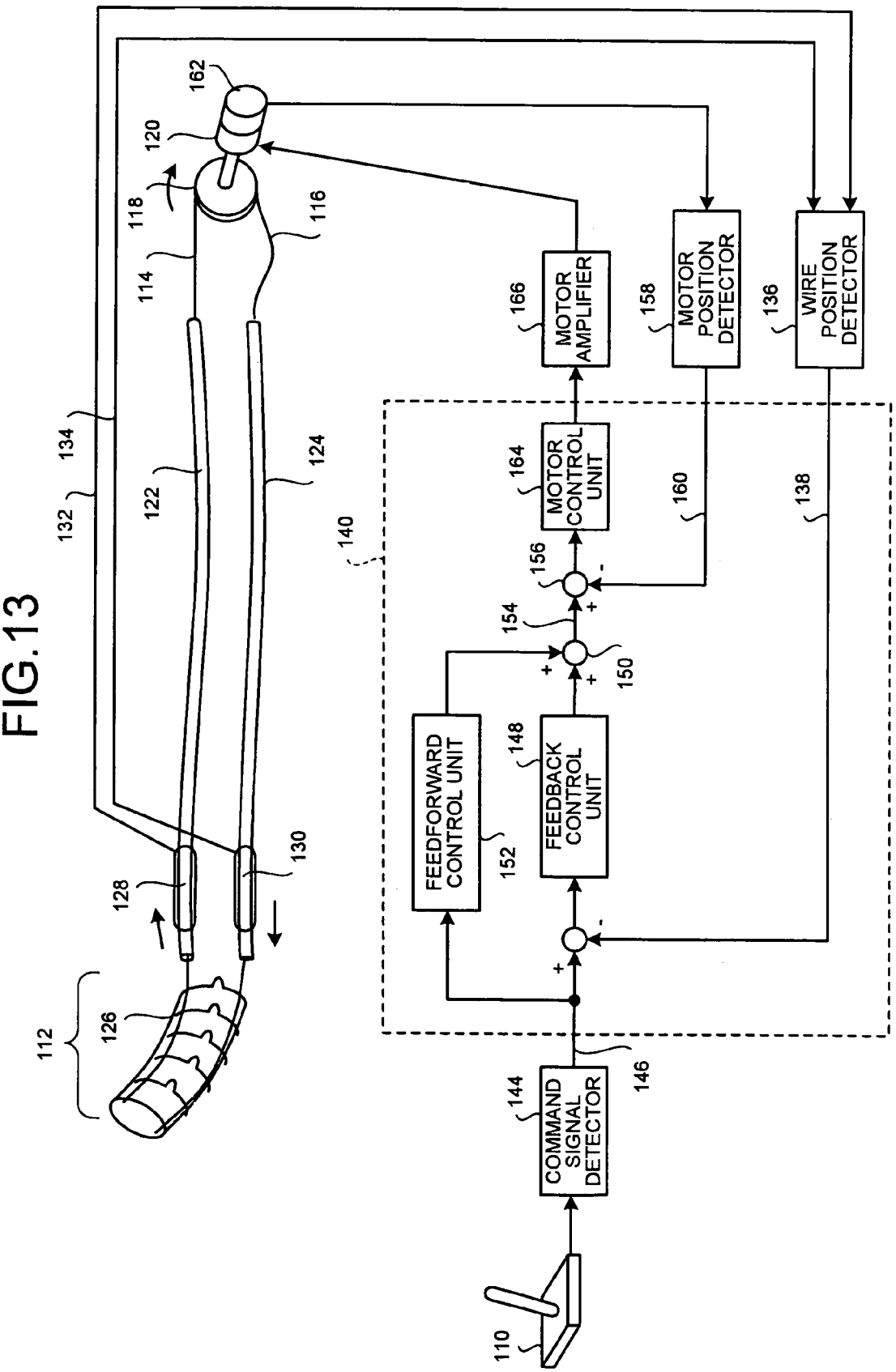

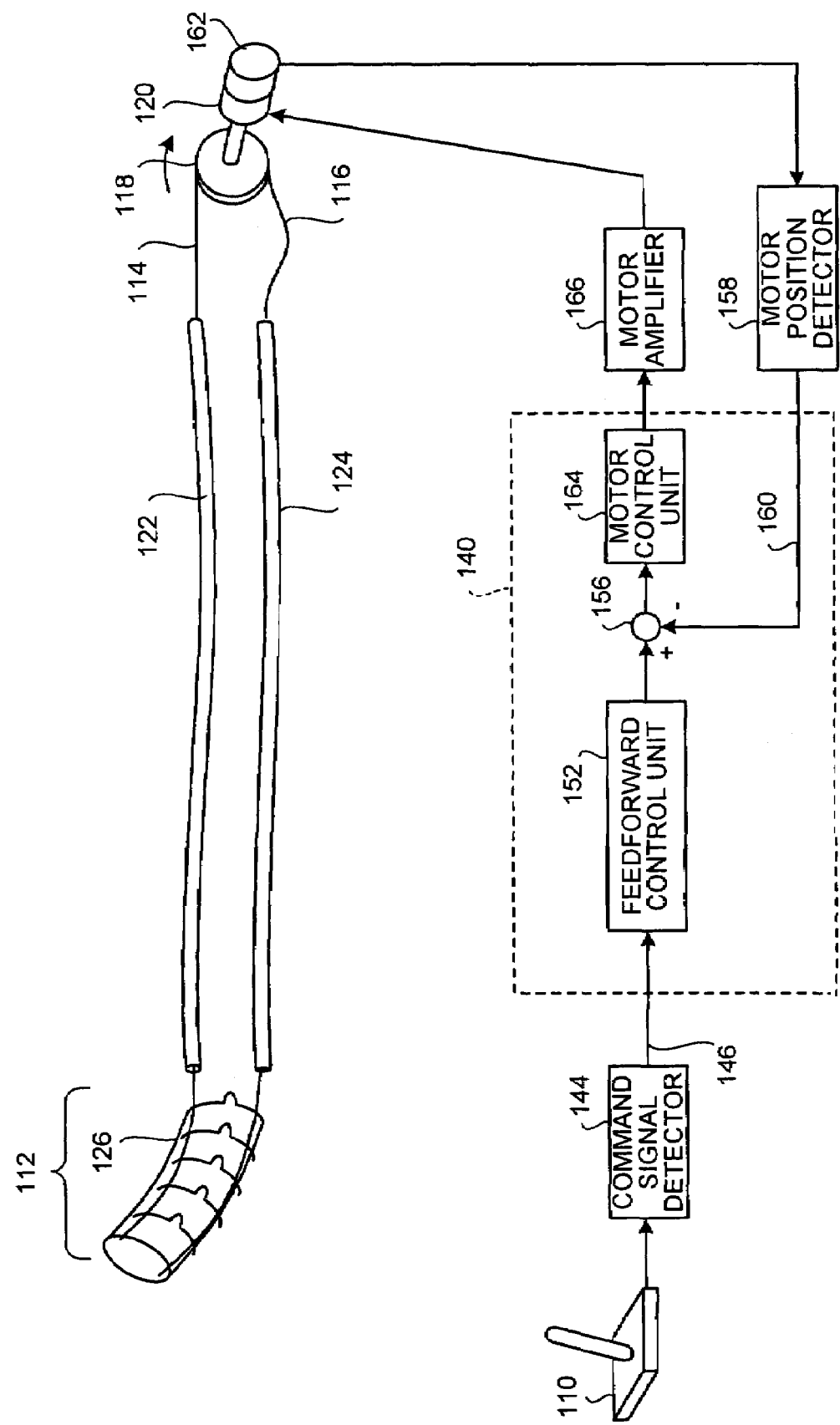

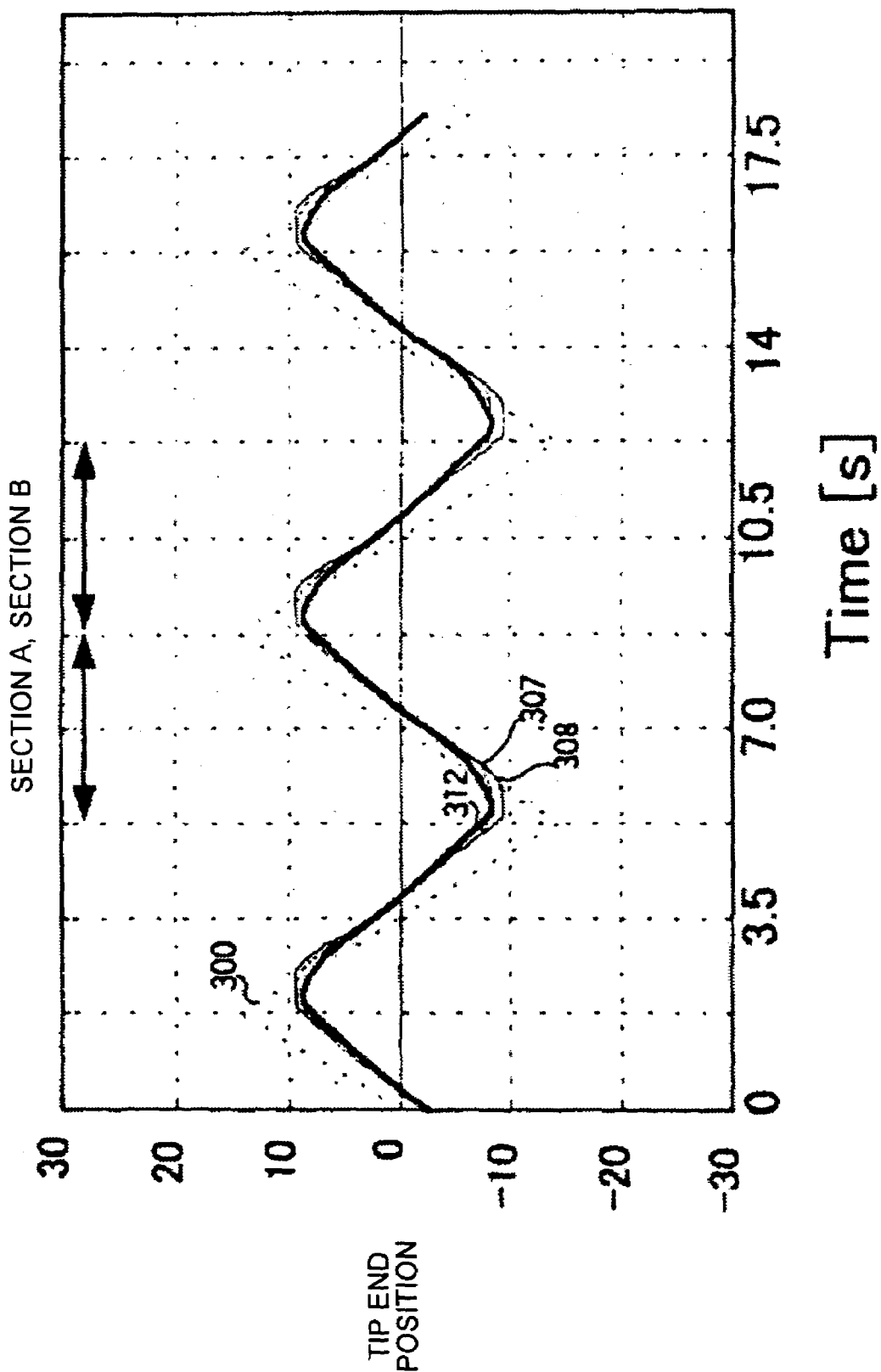

APPARATUS FOR DECIDING POSITION OF TRACTION

BACKGROUND OF THE INVENTION

1) Field of the Invention

The present invention relates to a technology for traction positional control for a motorized traction mechanism.

2) Description of the Related Art

A motorized traction mechanism for hauling a traction member such as a wire by operating a driving unit such as a motor, as in a motorized endoscope or a robot hand, to bend or rotate a distal tip is widely known. Since the motorized traction mechanism can be provided in such a manner that a generally large and heavy driving unit is separated from the distal tip via the traction member, there is a merit that the distal tip can be reduced in size and weight.

In the motorized traction mechanism, however, if the traction member in a bending or rotating state becomes loose, the distal tip does not respond until a slack is removed from the traction member.

A conventional endoscope that controls the slack of the wire is disclosed in, for example, Japanese Patent Application Laid-open No. 2000-300511. The conventional endoscope includes a flexible tube, a wire disposed in the flexible tube, a driving unit that drives the wire to for bend the flexible tube, a displacement detecting unit that detects a displacement from a reference position of the wire, a displacement direction detecting unit that detects a displacement direction of the wire, and a slack control Unit that controls the slack of the wire based on outputs of the displacement detecting unit and the displacement direction detecting unit. The conventional endoscope further includes a tension detecting unit that detects tension of the wire, and the slack control unit controls the slack of the wire based on outputs of the tension detecting unit, the displacement detecting unit and the displacement direction detecting unit.

In the conventional endoscope, a state of the slack is estimated based on displacement information and displacement direction information, and tension of wire detected by the tension detecting unit. In addition, the above publication discloses, as a concrete method for controlling the slack, that when the driving unit is driven to bend the flexible tube from an initial state (neutral reference position) in which both wire do not have the slack and any portion is not bent, one of the wire that is pushed out becomes loose, and when the driving unit is inverted and driven, assuming that the flexible tube can not be straightly bent by the loosened wire, a driving speed of the driving unit after the inversion is accelerated immediately after the inversion, and the speed is returned to the normal speed later.

However, in the conventional technology, there is no disclosure of controlling slack of the wire in a neutral reference position in the apparatus for traction positional control including both wires having the slack in the neutral reference position and characteristics that a flexible tube or wire tries to restore to an original state from a bent state.

Generally, when a distal bending section of an endoscope is operated, as described in Japanese Patent Publication No. S63-59329, a wire that is connected to the distal bending section is hauled by a driving force of an electric motor, thereby bending the distal bending section in vertical/lateral direction. When driving the electric motor, a voltage is applied to the motor in proportion to an operation amount of an operating lever provided on an operating section. In this case, by hauling the wire and moving the distal bending section vertically or laterally, a bending angle of the distal bending section can be set.

According to the conventional technology, the operation amount is determined based on a distortion gage mounted on the operating lever, and the voltage is directly applied to the motor in accordance with the operation amount. Therefore, although the electric motor can be driven in proportion to the operation amount of the operating lever, friction between the wire and an inner surface of a coil sheath for guiding the wire, and a slack of the wire are not sufficiently taken into account, the operation amount and a bending amount of the distal bending section do not correspond to each other, which is not sufficient for enhancing the operability of an observer (operator of the endoscope).

Japanese Patent Application Laid-open No. H6-22904 describes a technique in which a hauling wire is mounted to a distal bending section of an endoscope inserting portion, the hauling wire is allowed to pass through a universal cord through a relay pulley provided on the operating section, and the hauling wire is hauled by a driving force of the electric motor. It also discloses a technique in which a rotation angle of the pulley and a rotation angle of the electric motor are compared with each other, a loose state of the hauling wire is detected, and when the hauling wire is in a loosened state, the electric motor is driven at a maximum speed, and the slack of the hauling wire is instantaneously resolved.

In this conventional technology, the slack of wire generated in the universal cord between the motor and the relay pulley can be resolved, but slack and friction generated in the hauling wire of the endoscope inserting portion from the relay pulley are not taken into account, and a situation when the relay pulley does not exist is not taken into account, either.

SUMMARY OF THE INVENTION

It is an object of the present invention to solve at least the problems in the conventional technology.

The apparatus for traction positional control according to one aspect of the present invention includes a hauling unit that hauls a subject to bend or rotate the subject, a control unit that outputs a control signal, and a driving unit that drives the hauling unit based on the control signal. The control signal corresponds to a target value that is input by an operating unit. The control unit controls a variation amount of the control signal output in a predetermined range including a position of the hauling unit in a state before the hauling unit hauls the subject to be greater than a variation amount of the control signal output outside the predetermined range.

The apparatus for traction positional control according to another aspect of the present invention includes a wire that hauls a subject to bend or rotate the subject, a control unit that outputs a control signal, and a motor that drives the wire based on the control signal. The control signal corresponds to a target value that is input by a joystick. The control unit controls a variation amount of the control signal output in a predetermined range including a position of the wire in a state before the wire hauls the subject to be greater than a variation amount of the control signal output outside the predetermined range.

The apparatus for traction positional control according to still another aspect of the present invention includes a hauling unit that hauls a subject to bend or rotate the subject, an output unit that outputs an operation command value signal that corresponds to a target value that is input by an operating unit, a feedforward control unit that compensates the operation command value signal based on a feedforward compensation value, and generates a feedforward control signal, a drive control unit that generates a control signal based on the feedforward control signal, and a driving unit that drives the hauling unit based on the control signal.

The apparatus for traction positional control according to still another aspect of the present invention includes a hauling unit that hauls a subject to bend or rotate the subject, an output unit that outputs an operation command value signal that corresponds to a target value that is input by an operating unit, a feedforward control unit that compensates the operation command value signal based on a feedforward compensation value, and generates a feedforward control signal, a drive control unit that generates a control signal based on the feedforward control signal, a correction control unit that controls a variation amount of the control signal output in a predetermined range including a position of the hauling unit in a state before the hauling unit hauls the subject to be greater than a variation amount of the control signal output outside the predetermined range, and a driving unit that drives the hauling unit based on the control signal.

The other objects, features and advantages of the present invention are specifically set forth in or will become apparent from the following detailed descriptions of the invention when read in conjunction with the accompanying drawings.

BRIEF DESCRIPTION OF THE DRAWINGS

FIG. 13 is a schematic diagram of a motorized endoscope according to an eighth embodiment of the present invention;

FIG. 16 is a schematic diagram of a motorized endoscope according to a ninth embodiment of the present invention;

FIG. 21 is a graph of time-varying response waveform representing a result of estimation of the distal tip position according to the tenth embodiment;

DETAILED DESCRIPTIONS

Figure 1:
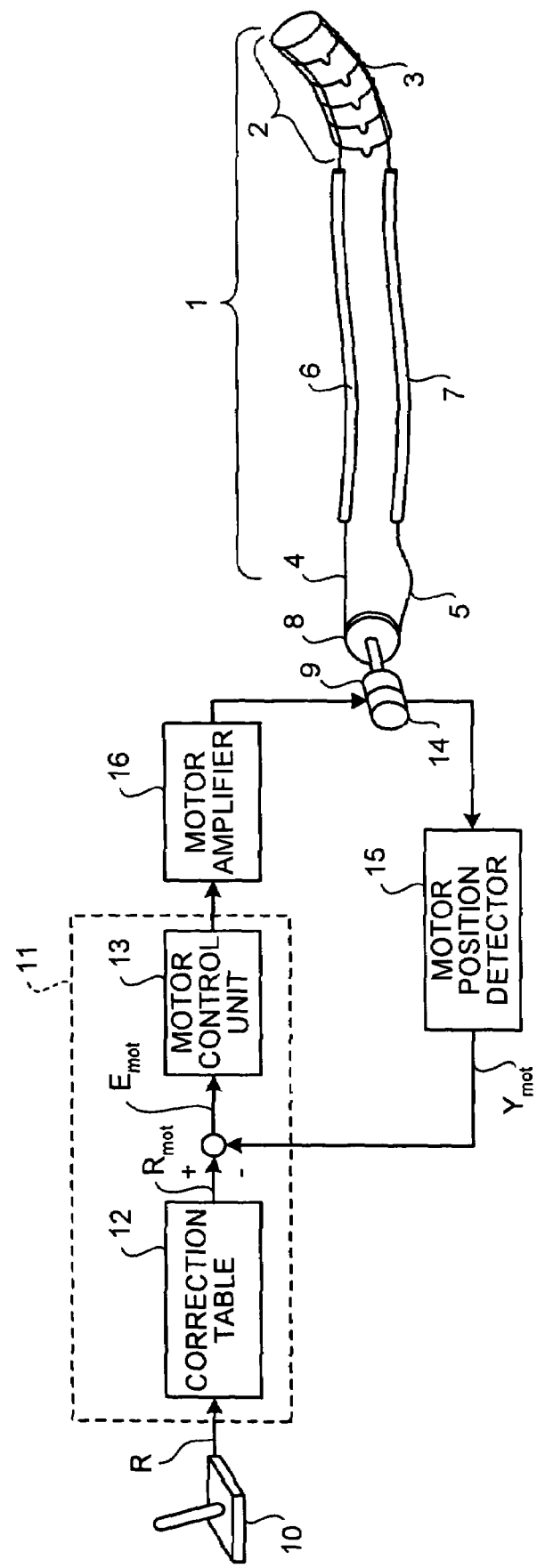
FIG. 1 is a schematic diagram of a motorized endoscope according to a first embodiment of the present invention.

Exemplary embodiments of an apparatus for traction positional control according to the present invention are explained with reference to the accompanying drawings. The same reference number in each embodiment represents the same or equivalent element. A case in which the invention is used for a motorized endoscope will be explained mainly, but the invention is not limited to the case in which the invention is used for the motorized endoscope, and the invention can also be used for other motorized traction mechanism such as a robot hand.

A motorized endoscope of a first embodiment of the present invention will be explained with reference to FIG. 1 to FIG. 5.

This motorized endoscope comprises a distal bending section 2 that can be bent and is a towed mechanism, wires 4 and 5 that are hauling units for hauling and bend the distal bending section 2 from both directions, a motor 9 that is driving unit that generates a driving force to the wires 4 and 5 in accordance with a control signal, a rotary encoder 14 that is a position detecting unit that detects a position of the motor 9, a joystick 10 that is an operating unit that inputs a target value, and a control device 11 that is a control unit that outputs a control signal that corresponds to the target value by the joystick 10 and that is based on a detected position detected by the rotary encoder 14.

An inserting portion 1 is formed into a thin and long shape so that the inserting portion 1 can be inserted into a body cavity or a pipe. The inserting portion 1 is provided at its tip end with the distal bending section 2, the wires 4 and 5 for bending the distal bending section 2 vertically and laterally, and coil sheaths 6 and 7 for protecting the wires 4 and 5. A pulley 8, the motor 9 and the control device 11 are provided outside the inserting portion 1.

The distal bending section 2 is a hose comprising a plurality of articulation wheels 3 that are rotatably connected to one another. FIG. 1 illustrates a state in which the distal bending section 2 is bent in the vertical direction. The distal bending section 2 has such characteristics that when a tension caused by the wires 4 and 5 is weakened from a state in which the distal bending section 2 is bent, the distal bending section 2 tries to restore to its original state to some degrees. The distal bending section 2 is provided at its tip end with one tip ends of the wires 4 and 5. The two wires 4 and 5 are made of flexible material, the wires 4 and 5 pass through the coil sheaths 6 and 7, and the other ends of the wires 4 and 5 are wound around the pulley 8 from opposite directions and fixed. The pulley 8 is connected to the motor 9 through a gear or the like (not illustrated), and constitutes a portion of the driving unit. That is, if the motor 9 is driven to rotate the pulley 8, the one wire 4 wound around the pulley 8 is pulled, and the other wire 5 is sent out. With this, the distal bending section 2 is bent upward.

FIG. 1 only illustrates a device for vertically bend the distal bending section 2 for simplifying the drawing. Since structure, operation and effect of wires, coil sheaths, a pulley, a motor and a control device for laterally bending the distal bending section 2 are basically the same as those of the device that vertically bends the distal bending section 2, these elements are omitted. Further, although it is not illustrated in the drawings, the inserting portion comprising a distal bending section, wire and coil sheaths are protected by a thin and long elastic pipe or the like.

The inserting portion 1 is usually provided at its leading end with a charge coupled device (CCD) (not illustrated) or the like, and with a monitor (not illustrated) on which an image of an organ in a body cavity or an interior of the pipe is displayed. An operator vertically and laterally bends and operates the distal bending section 2 by means of the joystick 10 while seeing an image displayed on the monitor. Therefore, if an operation amount of the joystick 10 and a bend angle of the distal bending section 2 coincide with each other, the operability is enhanced.

The control device 11 outputs a control signal for driving the motor 9 so that an operation amount of the joystick 10 is defined as a target value R, the target value R and the bend angle of the distal bending section 2 coincide with each other as close as possible. The control device 11 includes a correction table 12 having a previously prepared parameter, and a motor control unit 13 for driving the motor 9 based on a control signal Rmot that is output from the correction table 12. A rotary encoder 14 is mounted to the motor 9. An output of the rotary encoder 14 is detected by a motor position detector 15. A motor position signal Ymot is output from the motor position detector 15. The motor control unit 13 is for compensating a deviation Emot (=Rmot−Ymot) between the control signal Rmot and the motor position signal Ymot. For example, the motor control unit 13 comprises a PID (proportion, integration, differentiation) that is a known technique. The control signal that is output from the motor control unit 13 is amplified by a motor amplifier 16 and is input to the motor 9. With such a structure, the motor 9 can follow the control signal Rmot substantially without delay.

Since the motor 9 can follow the control signal Rmot substantially without delay, it is only necessary for the correction table 12 to compensate characteristics from the motor 9 to the bend angle of the distal bending section 2. In the motorized endoscope, none of the wires 4 and 5 does not become loose in a neutral reference position where the distal bending section 2 is not bent in the vertical direction. However, if the wires 4 and 5 extend with time, both the wires 4 and 5 become loose in some cases in an initial state (neutral reference position) in which the distal bending section 2 is not bent in the vertical direction. In such as state, even if attempt is made to bend the distal bending section 2 in any of upper and lower directions, the distal bending section 2 is not bent until the motor 9 is rotated to a position where the slack of the wire in that direction is resolved. The correction table 12 is arranged such that the table compensates characteristics in a predetermined range of the neutral reference position.

Figure 2:
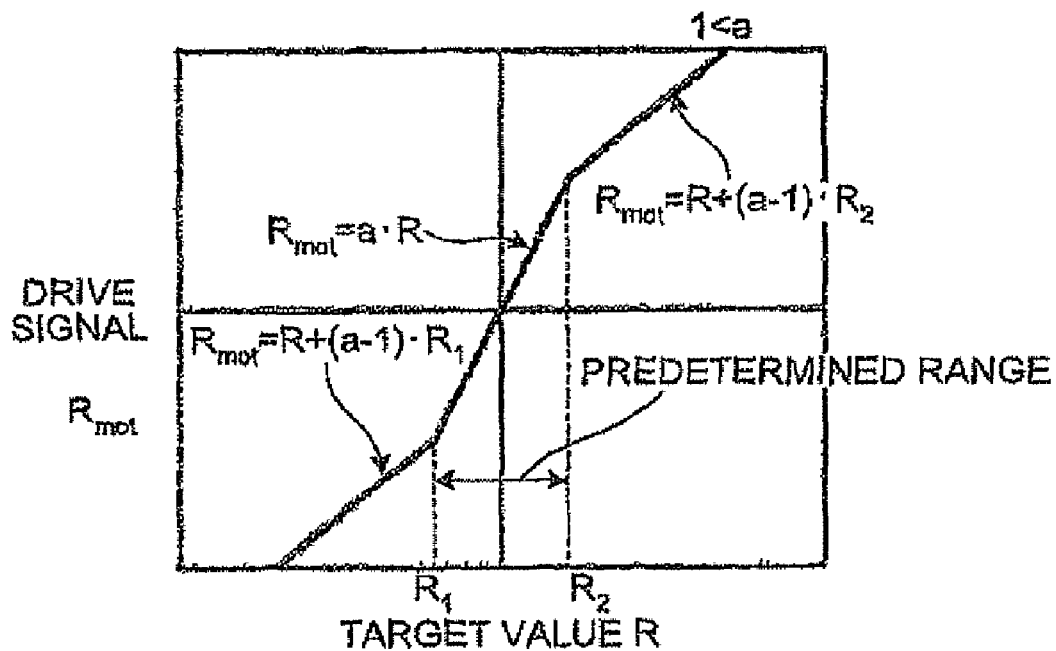
FIG. 2 is an example of characteristics of the correction table shown in FIG. 1.

More concretely, the correction table 12 is arranged as illustrated in the following equations (A) to (C):

$$\text{when } R<R1, Rmot=R+(a-1)\times R1 \quad (A)$$

$$\text{when } R1\leq R\leq R2, Rmot=a\times R \quad (B)$$

$$\text{when } R2<R, Rmot=R+(a-1)\times R2 \quad (C)$$

where a is a value greater than 1, R1 is a lower limit value in a range of target value R including the neutral reference position where both the wires 4 and 5 become loose, and R2 is an upper limit value in a range of target value R where both the wires 4 and 5 become loose. FIG. 2 illustrates characteristics of the correction table 12. An operation amount of the joystick 10 is defined as the target value R of the bend angle (position) of the distal bending section 2.

With such a structure, the correction table 12 outputs a control signal Rmot in which a variation amount thereof with respect to the target value R becomes greater in the target value R including the neutral reference position where both the wires 4 and 5 become loose than a range other than the range of the target value R, and the correction table 12 swiftly rotates the motor 9 and swiftly resolves the slack of the wires.

It is preferable that the lower limit value R1 and the upper limit value R2 are varied in accordance with degree of extension of the wires 4 and 5, but the lower limit value R1 and the upper limit value R2 may be set manually each time or may be set automatically by carrying out calibration at appropriate timing. When the lower limit value R1 and the upper limit value R2 are set automatically by carrying out calibration, it is necessary to mount tension sensor to the wires 4 and 5 to measure the slack of the wire. During the calibration, the target value R is automatically generated to bend the motorized endoscope, the slack of the wire is measured, a range of the target value R at which slack is generated in both the wires 4 and 5 is checked, and the lower limit value R1 and the upper limit value R2 are set.

The range of the target value R including the neutral reference position where slack is generated in both the wires 4 and 5 varies depending upon shape of the inserting portion 1, speed of the distal bending section 2 and the like. The lower limit value R1 and the upper limit value R2 can not completely coincide with the range of the target value R at which both the wires 4 and 5 actually become loose. If the target ranges R1 to R2 are smaller than an actual range, the compensation of the slack of the wire is insufficient, and if the target ranges R1 to R2 are greater than the actual range, speed of the distal bending section at a portion of the wire that is not loosened becomes excessively high in some cases. The lower limit value R1 and the upper limit value R2 are adjusted such that the operability is optimized while taking characteristics of the lower limit value R1 and the upper limit value R2 into account.

Figure 3:
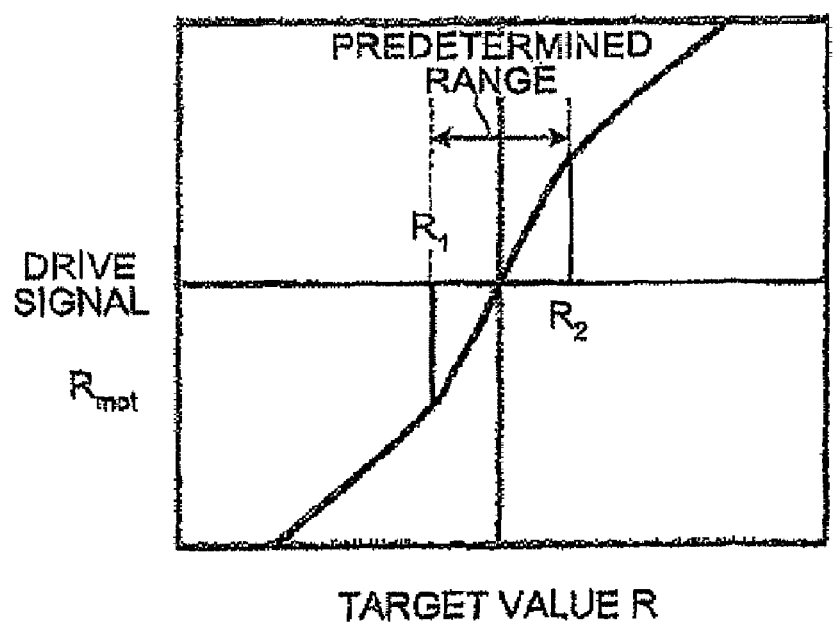
FIG. 3 is another example of characteristics of the correction table shown in FIG. 1.

An output of the correction table 12 need not be used as the control signal Rmot as it is, and the output may be allowed to pass through a notch filter or a low pass filter and then may be used as the control signal Rmot so that a differentiated value of the control signal Rmot is not abruptly varied. For the same reason, it is preferable that the correction table 12 has such characteristics that a variation amount of the control signal Rmot with respect to the target value R is continuously and smoothly varies from 1 to a as illustrated in FIG. 3.

Figure 4:
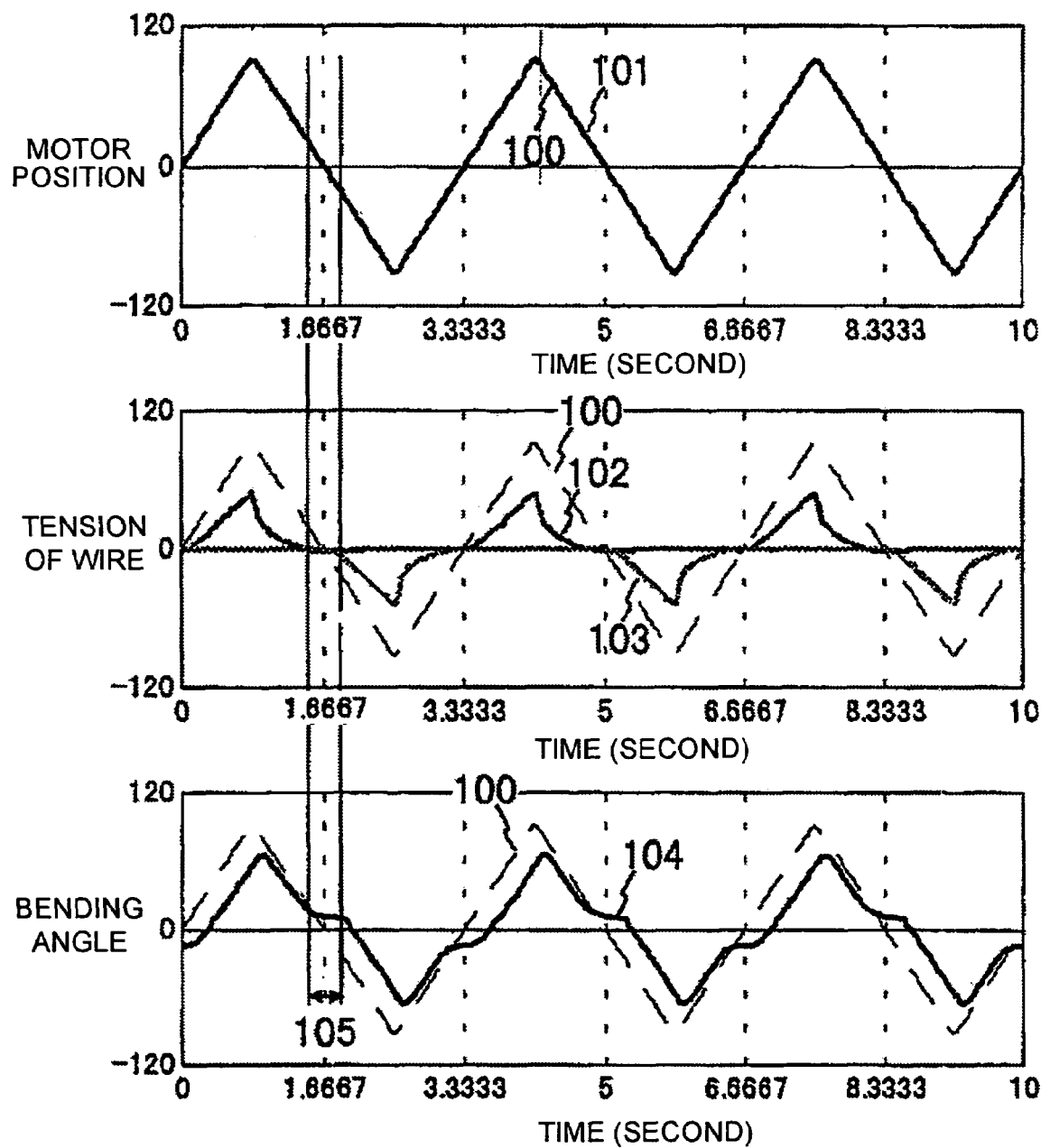
FIG. 4 are time-varying traces of motor position, wire tension, and angulation, respectively, when the correction table is not used.
Figure 5:
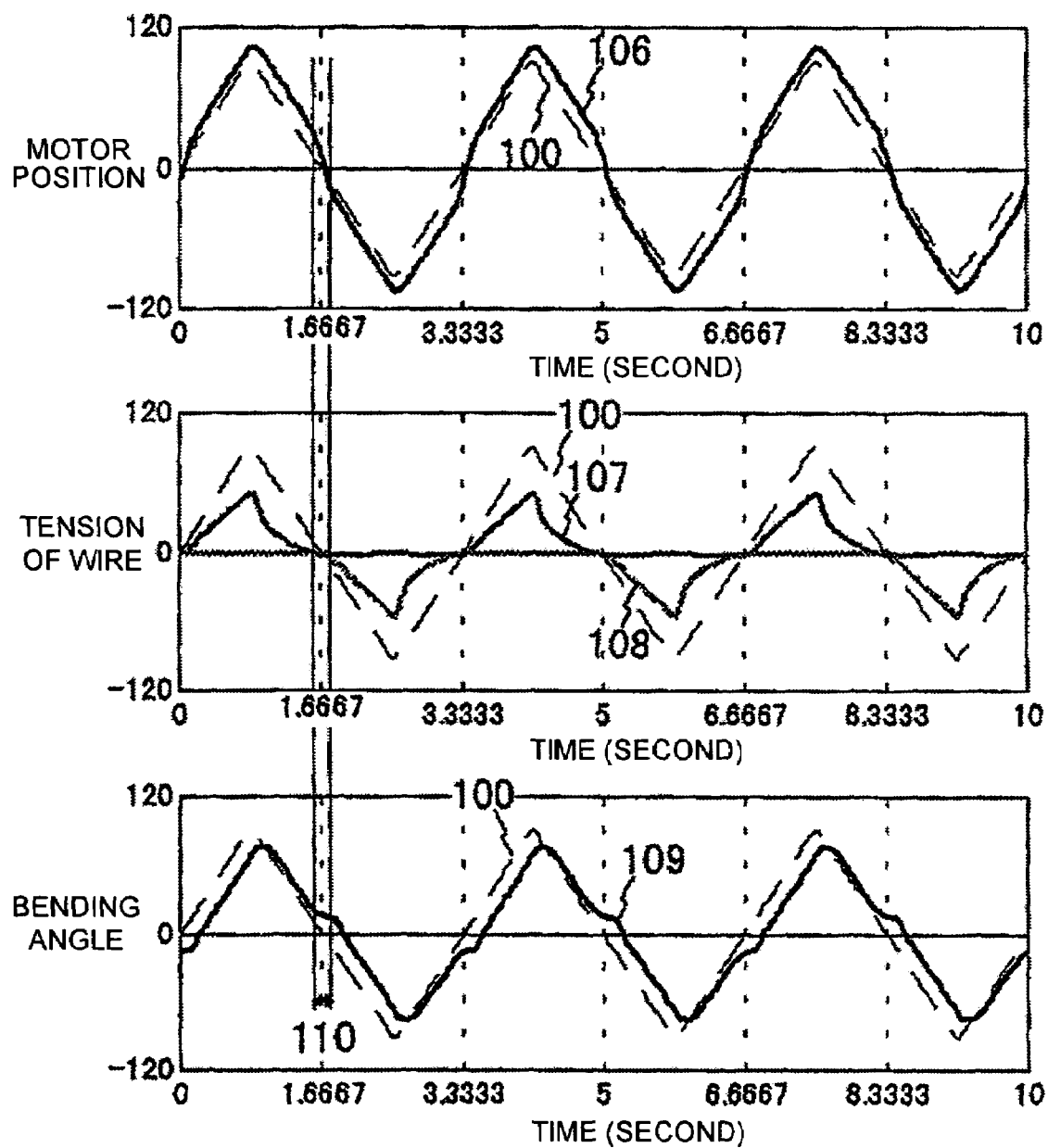
FIG. 5 are time-varying traces of motor position, wire tension, and angulation, respectively, when the correction table is used.

Referring to FIG. 4 and FIG. 5, effect of the first embodiment will be explained. FIG. 4 illustrates one example of a result of experiment when the correction table 12 illustrated in FIG. 1 is not used. FIG. 5 illustrates one example of a result of experiment when the correction table 12 illustrated in FIG. 1 is used. In this experiment, assuming that the operation amount of the joystick 10 is triangular wave, the triangular wave is given as a target value 100. In FIG. 4 and FIG. 5, the target value 100 and a motor position 101 are illustrated in upper graphs, the target value 100 and tension 102 of the wires 4 and 5 are illustrated in intermediate graphs, and the target value 100and time wave of a bend angle (direction of the tip end) 104 of the distal bending section 2 are illustrated in lower graphs. Although the tensions 102 of the wires 4 and 5 are always positive values, a tension 102 of the wire 5 for bending the distal bending section downward is indicated with a negative value so that the graphs can easily be seen in correspondence With the bend angle 104. The bend angle 104 is indicated as zero when the distal bending section is not bent in any of upward and downward directions, as a positive value when the distal bending section is bent upward, and as a negative value when the distal bending section is bent downward.

When the correction table illustrated in FIG. 4 is not used, the target value 100 and the motor position 101 coincide with each other as apparent from the upper graph in FIG. 4, and it can be found that the motor 9 follows the control signal without delay. As apparent from the intermediate graph of FIG. 4, tensions 102 and 103 of both the wires 4 and 5 are zero in the vicinity of location where the target value 100 becomes zero, and both the wires 4 and 5 become loose. In a range 105 where the slack is generated, the bend angle 104 is not varies almost at all as apparent from the lower graph in FIG. 4, and it is found that the distal bending section 2 does not respond to the target value 100.

On the other hand, when the correction table 12 illustrated in FIG. 5 is used, the motor position 106 is largely varied as apparent from the upper graph in FIG. 5 in a range 110 where the tensions 107 and 108 of both the wires 4 and 5 become zero illustrated in the intermediate graph in FIG. 5, and it can be found that the motor 9 is swiftly and largely rotate. As a result, time of the range 110 during which slack is generated is shorter than that in FIG. 4, and it can be found that the response of the distal bending section 2 is remarkably enhanced.

A second embodiment of the present invention will be explained with reference to FIG. 6. The second embodiment is different from the first embodiment in the following description, and other portions of the second embodiment are basically the same as those of the first embodiment.

In this second embodiment, the operation amount of the joystick 10 is defined as a target value R' of speed of the distal bending section 2. That is, an operator designates the speed of the distal bending section 2, and operates the apparatus. In the second embodiment, an integrator 17 is provided in front of the correction table 12, and a value to be input to the correction table 12 is defined as a target value R of position of the distal bending section 2 like the first embodiment. A differentiator 18 is provided behind the correction table 12, a control signal Rmot that is output from the correction table 12 is differentiated, and the resultant is defined as a speed control signal Rmot'. A motor speed detector 19 is provided instead of the motor position detector 15 illustrated in FIG. 1, so that a motor speed signal Ymot' can be obtained. The motor control unit 13 compensates a deviation Emot' (=Rmot'−Ymot') between the speed control signal Rmot' and the motor speed signal Ymot'.

The same effect as that of the first embodiment can be obtained by the second embodiment.

A third embodiment of the present invention will be explained with reference to FIG. 7 and FIG. 8. The third embodiment is different from the first embodiment in the following description, and other portions of the third embodiment are basically the same as those of the first embodiment.

In the third embodiment, ranges R1 to R2 of the target value R at which both the wires 4 and 5 become loose is automatically renewed. In this third embodiment, tension sensors 20 and 21 are mounted to the wires 4 and 5 as illustrated in FIG. 7, and a wire tension detector 22 detects tensions T1 and T2 (both tensions are zero or higher). The renewal unit 23 renews the lower limit value R1 and the upper limit value R2 using the motor position signal Ymot and the tensions T1 and T2 of the wires 4 and 5. If it is judged that slack is generated in both the wires 4 and 5 and the motor 9 is not abruptly driven even if the lower limit value R1 and the upper limit value R2 are renewed, the renewal unit 23 substitutes the current R into the lower limit value R1 or the upper limit value R2.

The operation of the renewal unit 23 will be explained with reference to FIG. 8.

In step S1, it is judged whether slack is generated in both the wires 4 and 5. If it is judged that slack is generated in both the wires 4 and 5, since T1=T2=0, if T1+T2=0, this unit that slack is generated in both the wires 4 and 5 (because both T1 and T2 are zero or higher). However, if the precision of the tension sensors 20 and 21 is taken into account, T1+T2 is not always zero completely. Therefore, when T1+T2 becomes lower than T0 using previously set small positive value T0, it is judged that slack is generated in both the wires 4 and 5. If it is judged that slack is generated in both the wires 4 and 5, the procedure is proceeded to next step S2, and if it is not judged so, the lower limit value R1 and the upper limit value R2 are not renewed.

In step S1, when both T1<T01 and T2<T02 are established using small positive values T01 and T02, it may be judged that slack is generated in both the wires 4 and 5.

In step S2, it is judged whether a current motor position signal Ymot and a control signal Rmot when the lower limit value R1 and the upper limit value R2 are renewed are substantially the same so that the motor 9 is not abruptly driven by renewing the lower limit value R1 and the upper limit value R2. Because a control signal when the lower limit value R1 and the upper limit value R2 are renewed can be expressed as a×R, it is judged whether |Ymot−a×R| is smaller than the preset small positive value ϵ. If |Ymot−a×R| is smaller than ϵ, the procedure is proceeded to next step S3 for renewing the lower limit value R1 or the upper limit value R2, and if |Ymot−a×R| is not smaller than ϵ, the lower limit value R1 and the upper limit value R2 are not renewed.

Because the current motor position signal Ymot is substantially the same as a control signal only a short while ago (before one sampling), a control signal only a short while ago (before one sampling) may be used instead of the motor position signal Ymot in step S2.

In step S3, it is judged which one of the lower limit value R1 and the upper limit value R2 should be renewed. If a target value at which the distal bending section 2 is not bent in any of upward and downward directions is defined as zero, arrange of a target value at which both the wires 4 and 5 become loose is R1<0 and R2>0 because the range straddles zero. Therefore, when R>0, a current R is assigned to the upper limit value R2, and otherwise, the current R is assigned to the lower limit value R1. The lower limit value R1 and the upper limit value R2 are renewed using these methods illustrated in FIG. 8.

When it is assumed that |R1|=|R2| and the lower limit value R1 is renewed, the upper limit value R2 may be also renewed to a value of −R1, and when the upper limit value R2 is renewed, the upper limit value R1 may be also renewed to a value of −R2.

A range of the target value R at which both the wires 4 and 5 become loose depends shape of the inserting portion and speed of the distal bending section, but if the third embodiment is used, the lower limit value R1 and the upper limit value R2 can be renewed. Therefore, it is possible to enhance the response of the distal bending section under a condition close to an actual using condition.

Figure 9:
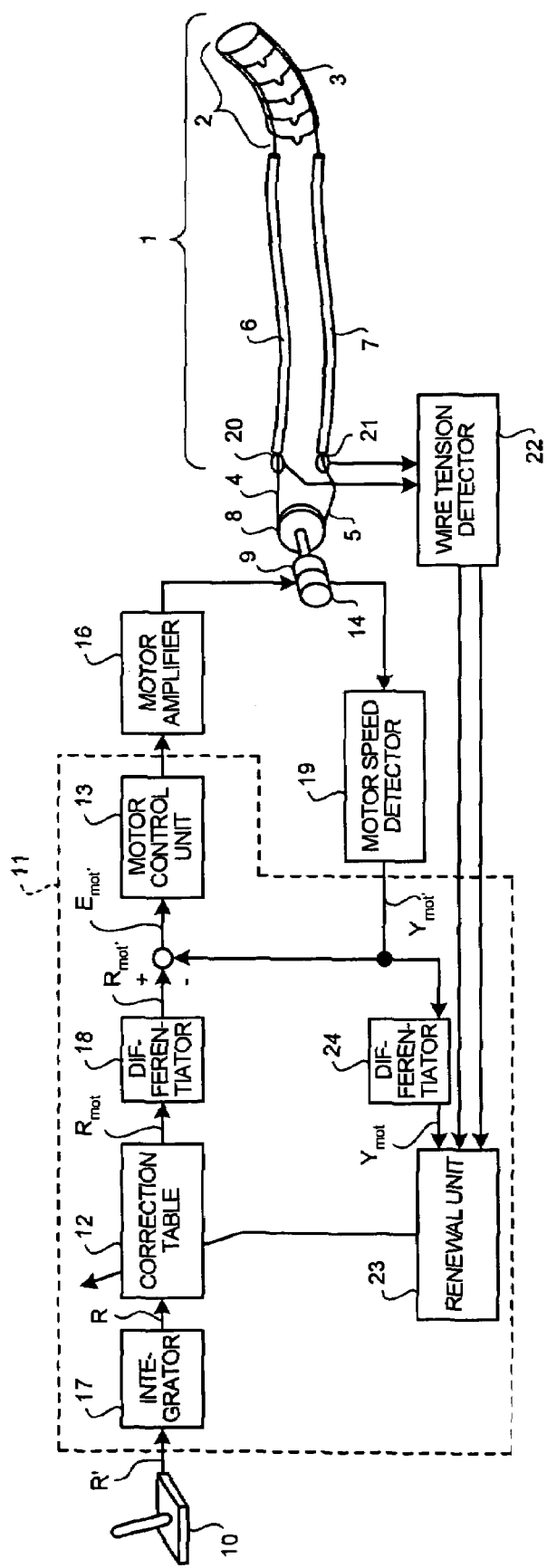
FIG. 9 is schematic diagram of a motorized endoscope according to a fourth embodiment of the present invention.

A fourth embodiment of the present invention will be explained with reference to FIG. 9. The fourth embodiment is different from the third embodiment in the following description, and other portions of the third embodiment are basically the same as those of the third embodiment.

In the fourth embodiment, the operation amount of the joystick 10 is defined as target value R' of speed of the distal bending section 2. In this fourth embodiment, an integrator 17 is provided in front of the correction table 12, and a value to be input to the correction table 12 is defined as a target value R of a position of the distal bending section 2 like the third embodiment. A differentiator 18 is provided behind the correction table 12, a control signal Rmot that is output from the correction table 12 is differentiated, and the resultant is defined as a speed control signal Rmot'. A motor speed detector 19 is provided instead of the motor position detector 15 illustrated in FIG. 7, and the motor control unit 13 compensates a deviation Emot' (=Rmot'−Ymot') between the speed control signal Rmot' and the motor speed signal Ymot'. An integrator 24 is provided between the motor speed detector 19 and the renewal unit 23 so that a motor position signal Ymot is input to the renewal unit 23.

The same effect as that of the third embodiment can be obtained also by this fourth embodiment.

Figure 10:
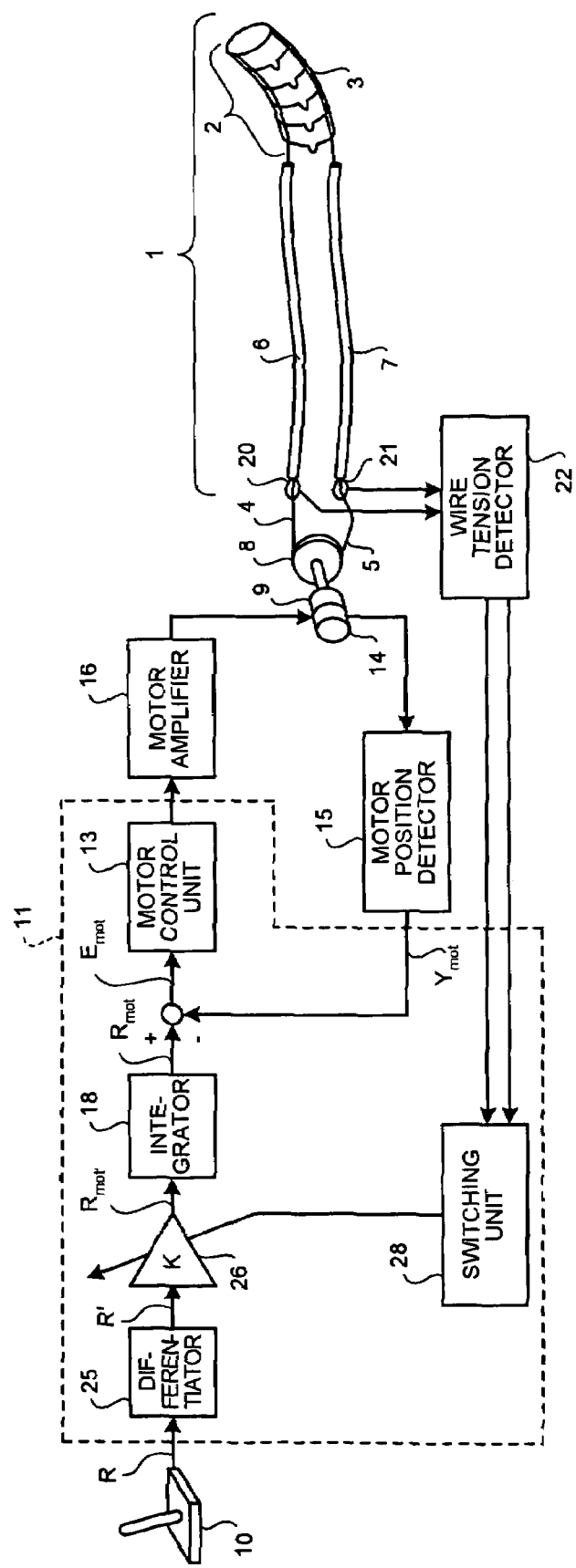
FIG. 10 is a schematic diagram of a motorized endoscope according to a fifth embodiment of the present invention.

A fifth embodiment of the present invention will be explained with reference to FIG. 10. The fifth embodiment is different from the third embodiment in the following description, and other portions of the fifth embodiment are basically the same as those of the third embodiment.

Figure 7:
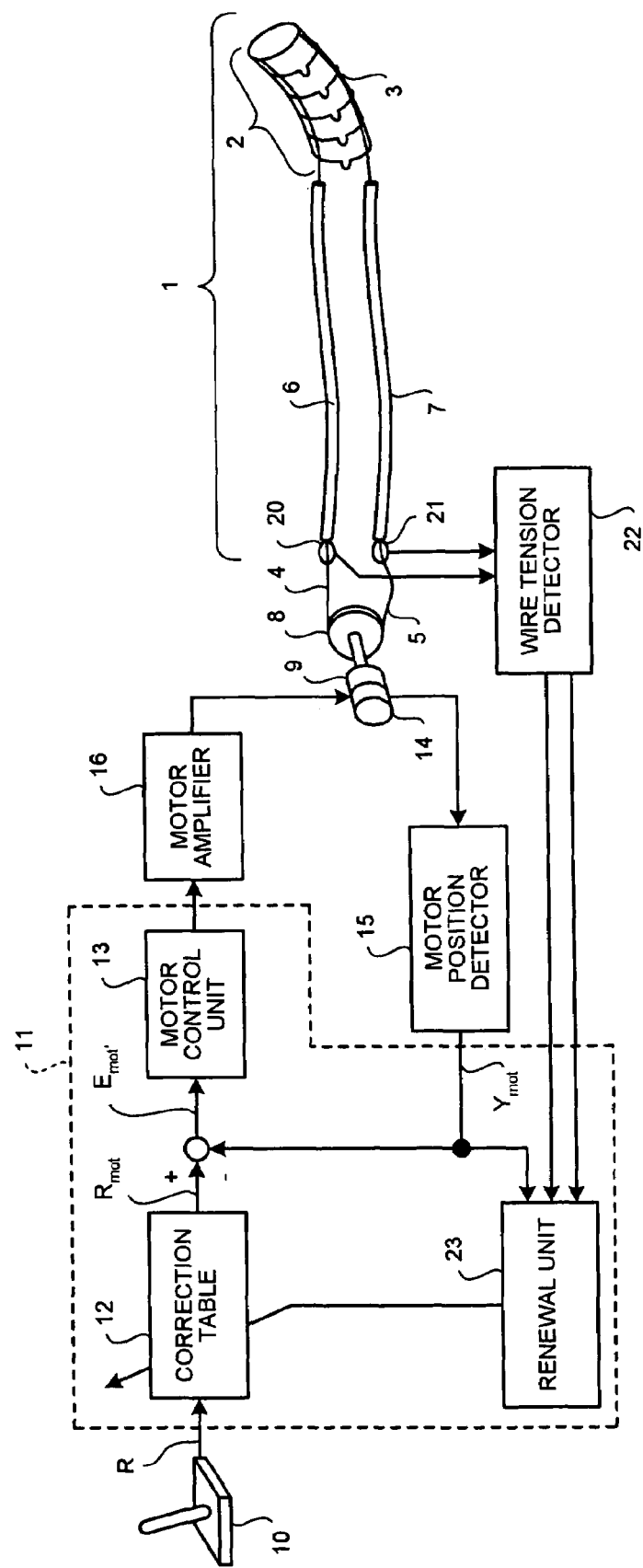
FIG. 7 is a schematic diagram of a motorized endoscope according to a third embodiment of the present invention.
Figure 8:
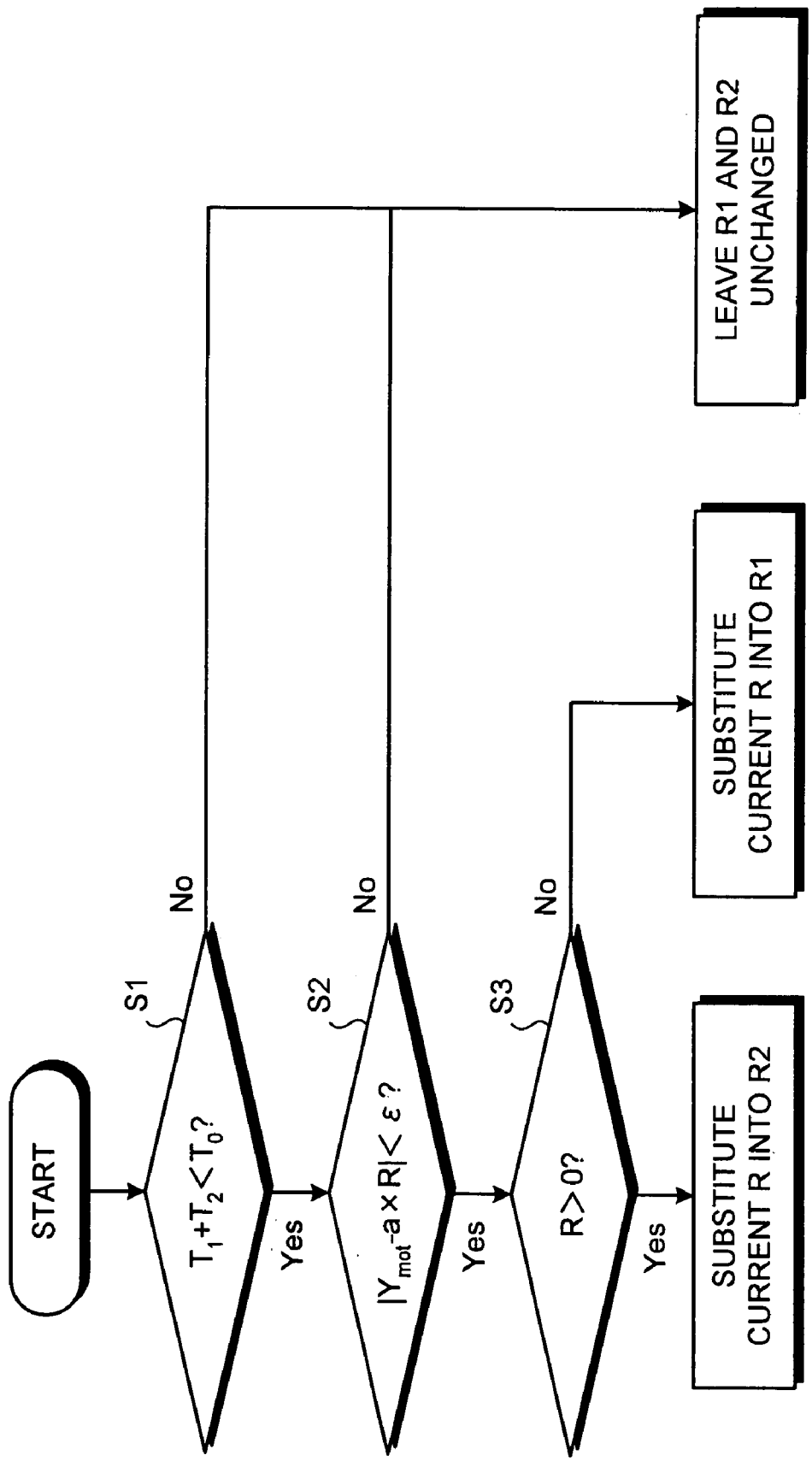
FIG. 8 is a flowchart of operation of a renewal unit of the motorized endoscope shown in FIG. 7.

According to the fifth embodiment, in FIG. 7 illustrating the third embodiment, the correction table 12 is replaced by a differentiator 25, a variable gain 26 and an integrator 27, and the renewal unit 23 is replaced by a switching unit 28. The correction table 12 determines a control signal Rmot from the target value R of position, but the variable gain 26 in the fifth embodiment determines a speed control signal Rmot' from a target value R' of speed.

The differentiator 25 differentiates the target value R of position that is output from the joystick 10, and outputs the target value R' of speed. The variable gain 26 multiplies the target value R' by k and outputs the resultant as speed control signal Rmot'. Here, k is determined by the switching unit 28. If both the wires 4 and 5 become loose, the switching unit 28 sets k to a which is greater than 1, and if not, the switching unit 28 sets k to 1. It is judged whether both the wires 4 and 5 become loose by the same method as that of the third embodiment. That is, when T1+T2<T0 is established or when both T1<T01 and T2<T02 are established, it is judged that both the wires 4 and 5 become loose. The integrator 27 integrates the speed control signal Rmot' and outputs a control signal Rmot.

In order to prevent a differentiated value of a control signal Rmot from being abruptly varied, an output of the integrator 27 may be allowed to pass through a notch filter or a low pass filter and then the resultant may be used as the control signal Rmot, instead of using the output of the integrator 27 as the control signal Rmot as it is. For the same reason, the switching unit 28 may determine k such that k is continuously varied from 1 to a in accordance with tensions of the wires 4 and 5.

The same effect as that of the third embodiment can be obtained also by this fifth embodiment.

A sixth embodiment of the present invention will be explained with reference to FIG. 11. The sixth embodiment is different from the fifth embodiment in the following description, and other portions of the sixth embodiment are basically the same as those of the fifth embodiment.

In the sixth embodiment, an operation amount of the joystick 10 that is determined as the target value R of position of the distal bending section 2 in the fifth embodiment is determined as a target value R' of speed of the distal bending section 2. With this structure, the differentiator 25 and the integrator 27 in FIG. 10 that illustrates the fifth embodiment become unnecessary. A motor speed detector 19 is provided instead of the motor position detector 15 illustrated in FIG. 10, and the motor control unit 13 compensates a deviation Emot' (=Rmot'−Ymot') between the speed control signal Rmot' and the motor speed signal Ymot'.

The same effect as that of the fifth embodiment can be obtained also by this sixth embodiment.

Figure 11:
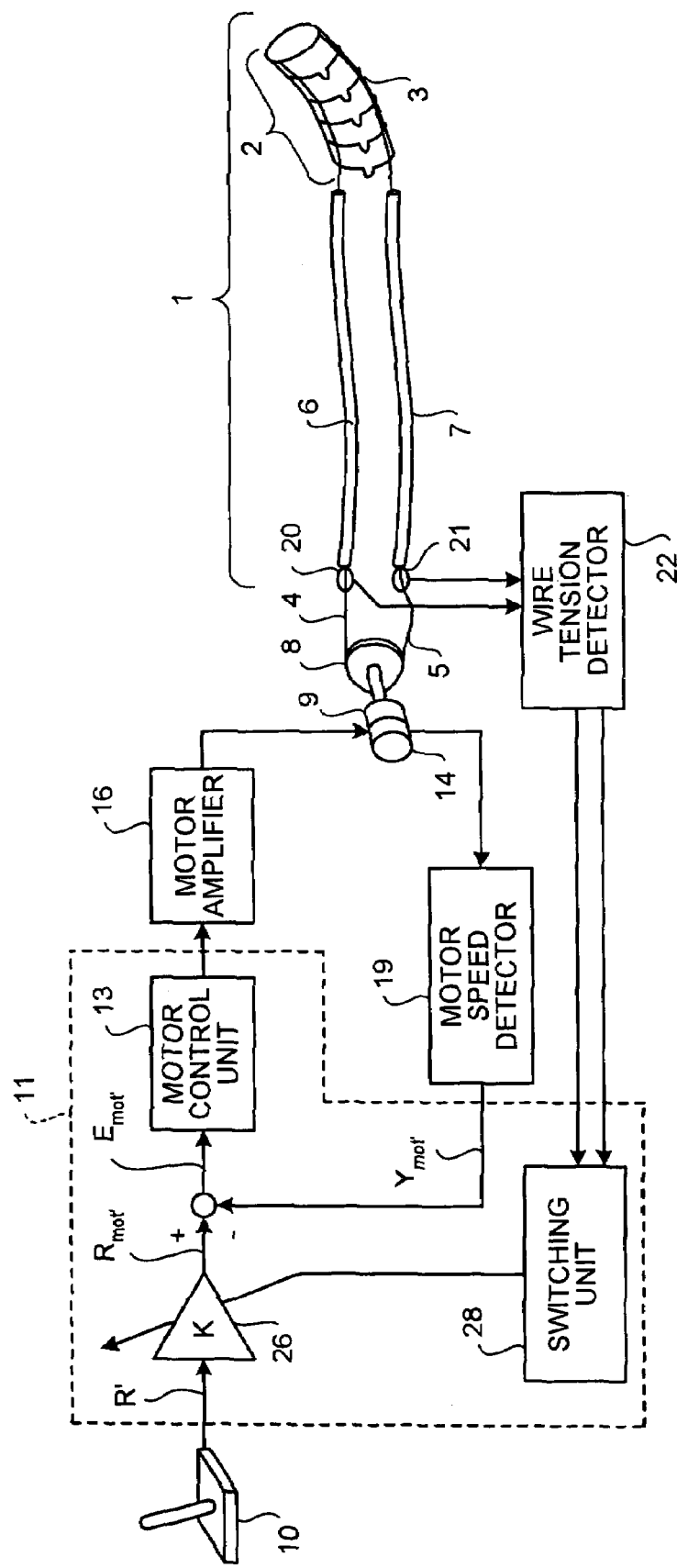
FIG. 11 is a schematic diagram of a motorized endoscope according to a sixth embodiment of the present invention.

The switching unit 28 illustrated in FIG. 11 may judge whether the wire 4 or 5 becomes loose and may determine k while taking only the wire 4 or 5 that is to be bent into account, instead of judging whether both the wires 4 and 5 become loose. If k is increased when the wire 4 or 5 that is to be bent becomes loose, slack generated when a bending direction is switched can be compensated, and the response of the distal bending section at that time can be enhanced.

A seventh embodiment of the present invention will be explained with reference to FIG. 12. The seventh embodiment is different from the first embodiment in the following description, and other portions of the seventh embodiment are basically the same as those of the fifth embodiment.

In the seventh embodiment, the apparatus for traction positional control of the first embodiment is applied to a robot hand. The robot hand comprises a driven section 29 provided at a tip end of the robot hand, wires 4 and 5 for rotating the driven section 29, coil sheaths 6 and 7 for protecting the wires 4 and 5, and a pulley 8, a motor 9, a joystick 10 and a control device 11 that function as driving sections.

A finger 30 is fixed to the driven section 29. If the driven section 29 is rotated, the finger 30 moves in the vertical direction. One tip ends of the wires 4 and 5 are wound around the driven section 29 from opposite sides and fixed thereto. The wires 4 and 5 pass through the coil sheaths 6 and 7, and the other ends of the wires 4 and 5 are wound around the pulley 8 from opposite sides and fixed thereto. The pulley 8 is connected to the motor 9 through a gear (not illustrated). If the motor 9 is driven to rotate the pulley 8, the driven section 29 rotates and the finger 30 moves. In the case of the robot hand, unlike the endoscope, a portion between the driven section 29 and the pulley 8 need not be soft or flexible in some cases. In that case, the coil sheaths 6 and 7 are not always necessary.

Figure 12:
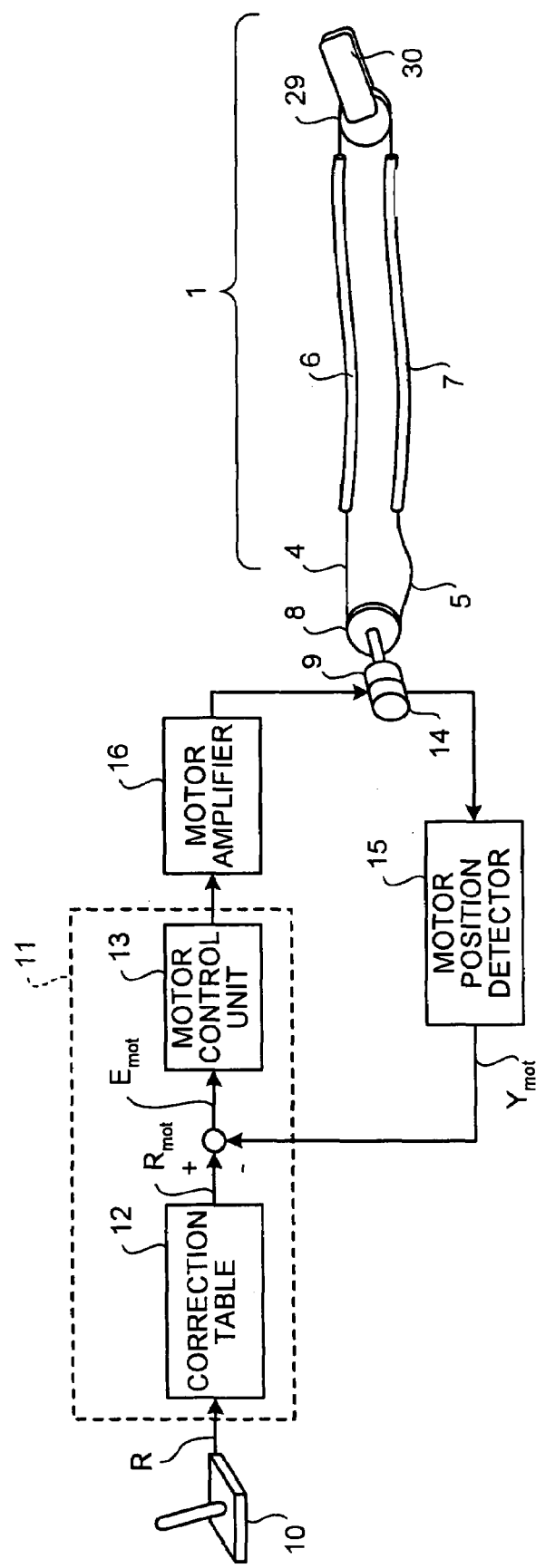
FIG. 12 is a schematic diagram of a robot hand according to a seventh embodiment of the present invention.

In FIG. 12, one more identical apparatus may be provided below the original apparatus, and the lower finger may grasp or release an object by moving the lower finger in an opposite manner from the upper finger. In that case, the joysticks 10 and the control devices 11 of the upper and lower apparatuses may be the same and the rotational directions of the pulleys 8 may be opposite from each other. The finger 30 may be provided at its tip end with a traction mechanism or other mechanism. The target value R may be generated automatically using a computer or the like instead of the joystick 10.

With such a robot hand, a problem of wire slack is generated like the endoscope, but the same effect as that of the motorized endoscope can be obtained also by the structure illustrated in FIG. 12.

Similarly, the second embodiment to the sixth embodiment can also be applied to a robot hand.

According to the apparatus for traction positional control of each of the first embodiment to the seventh embodiment, even if both the hauling units become loose at the neutral reference position, the slack can be controlled at the neutral reference position and it is possible to position the towed mechanism swiftly and precisely.

FIG. 13 illustrates a block diagram of an apparatus for controlling traction of a motorized endoscope according to an eighth embodiment of the present invention. In FIG. 13, the motorized endoscope is provided with a joystick 110 mounted to the operating section and capable of moving in the vertical and lateral directions, a distal bending section 112 that can be bent, hauling wires 114 and 116 for bending a tip end of the distal bending section 112 in the vertical direction, a pulley 118 around which the hauling wires 114 and 116 are wound and the pulley 118 applying a hauling force, and a motor (electric motor) 120 connected to the pulley 118 through a gear mechanism for rotating the pulley 118. The hauling wires 114 and 116 comprise one continuous wire and pass through coil sheaths 122 and 124 and are connected to the distal bending section 112. The distal bending section 112 is a to-be-operated subject that constitute a main element of the towed mechanism. The distal bending section 112 is a hose comprising a plurality of articulation wheels 126 that are rotatably connected to one another. The distal bending section 112 is formed into a substantially cylindrical shape, and can bend in the vertical and lateral directions.

The distal bending section 112 bends in the vertical direction by hauling the hauling wires 114 and 116. More specifically, if the motor 120 is rotated normally or reversely and the pulley 118 is rotated, one of the hauling wires 114 and 116 is pulled, the other is sent out and the distal bending section 112 bent in the vertical direction. That is, the hauling wires 114 and 116 are hauling units that haul the distal bending section 112 that is to be operated by driving the motor 120.

FIG. 13 only illustrates the pair of hauling wires 114 and 116 for vertically bending the distal bending section 112 for simplifying the drawing. Since the hauling wires, the pulley, the motor and the control device that are necessary to bending the distal bending section 112 in the lateral direction are the same as those used for vertically bending the distal bending section 112, illustration thereof is omitted.

The distal bending section 112 and the coil sheaths 122 and 124 are inserted into and protected by inserting portions (not illustrated) comprising thin and long elastic pipes. A CCD camera (not illustrated) comprising CCD is mounted to a tip end of the distal bending section 112 that is a tip end of the inserting portion. The CCD camera is connected to a monitor (not illustrated) through a cable disposed in the inserting portion. An image of an organ in a body cavity or an industrial pipe is displayed on a screen of the monitor. In this case, an operator operates the joystick 110 to bend the distal bending section vertically or laterally using his or her left hand while seeing the image displayed on the screen of the monitor, and holds an intermediate portion of the inserting portion with his or her right hand to move the inserting portion forward and backward, and some times rotates the inserting portion to push the inserting portion into the body cavity, and after the tip end of the inserting portion reaches a portion to be observed, the operator bends the tip end of the distal bending section 112 to shoot the observing point in an appropriate state, and can carry out appropriate processing using a tool inserted into the inserting portion.

Since the operator can observe, in real time, motion seen from the tip end of the inserting portion while seeing the monitor, if the operator can appropriately control the motor 120 and can freely control the motion of the tip end of the distal bending section 112, a load to the operator is reduced, and the operability is largely enhanced.

In the endoscope that is electrically driven by the wire, the tip end side distal bending section 112 of the inserting portion is hauled by the hauling wires 114 and 116 in accordance with a driving force of the motor. When the distal bending section 112 is hauled, degrees of the slack and friction between the hauling wires 114 and 116 and the coil sheaths 122 and 124 are varied by variation in friction between the hauling wires 114 and 116 and the coil sheaths 122 and 124, slack generated in the hauling wire that is not hauled by the pulley 118 (hauling wire that is sent out), and bending shape in the intermediate portion of the inserting portion. That is, if problems of friction, slack and variation in characteristics are not overcome, the bend position of the distal bending section 112 can not be allowed to follow the operation command value instantaneously.

Hence, in the eighth embodiment, using a feedforward control system that advances a phase of the operation command value, dynamics from a pulley position where the phase delays to a position of a tip end of the hauling wire 114 or 116 are moved, and a following error that can not completely be compensated by the feedforward control system is compensated by a feedback control system.

More specifically, a control system including the feedforward control system and the feedback control system is constructed as follows:

First, when the feedback control system is constructed, in the eighth embodiment, sensors 128 and 130 for observing the moving amounts of the hauling wires 114 and 116 are mounted to tip ends of the coil sheaths 122 and 124. The sensors 128 and 130 detect the moving amounts of the hauling wires 114 and 116 by means of an optical linear encoder, and a resistive linear potentiometer for example. In this case, since a distance from each the sensor 128, 130 to the tip end of the distal bending section 112 is shorter than the entire length of the inserting portion, positions of the hauling wires 114 and 116 detected by the sensors 128 and 130 are equal to a moving amount of a tip end of the distal bending section 112, i.e., the bend position. Wire position signals 132 and 134 detected by the sensors 128 and 130 are input to the wire position detector 136. In this case, the wire position signals 132 and 134 illustrate positive value when the hauling wires 114 and 116 move in the direction shown with arrows. The wire position detector 136 obtains the average of the sum of the wire position signals 132 and 134, and outputs the wire tip end position signal 138 in which the average value indicates a position of the tip end of the distal bending section 112.

That is, the sensors 128 and 130 and the wire position detector 136 are bend position detecting units that detect displacement caused when hauling the hauling wires 114 and 116 together with the hauling amount detecting unit, and output the wire tip end position signal 138 corresponding to the bend position of the distal bending section 112 as a hauling property detecting signal.

The wire tip end position signal 138 is input to an adder 142 of a controller 140. A command value signal 146 has been input to the adder 142 from a command signal detector 144. The command signal detector 144 is constructed as an output unit for operation command value signal. When the joystick 110 is operated in the vertical direction or lateral direction, the output unit for operation command value signal responds the operation of the joystick 110, and outputs a command value signal (operation command value signal) 146. The adder 142 is constructed as a command signal(property deviation calculating unit. The command signal (property deviation calculating unit calculates a deviation between the command value signal 146 and the tip end position signal 138, and outputs a signal concerning the calculated deviation to the feedback control unit 148. The feedback control unit 148 is constructed as a feedback control signal generation unit. The feedback control signal generation unit compensates only gain with respect to the deviation obtained by the adder 142, and generates a feedback control signal that suppresses the deviation to zero, and outputs the feedback control signal to an adder 150.

A feedforward signal is input to the adder 150 from a feedforward control unit 152. The feedforward control unit 152 is constructed as a feedforwad control signal generation unit. When the command value signal 146 is input from the command signal detector 144, the feedforward control signal generation unit carries out calculation for compensating the command value signal 146 in accordance with a feedforward compensation value as processing for advancing a phase of the command value signal 146, and generates a feedforward control system as a result of this calculation. More specifically, the feedforward control unit 152 comprises a secondary phase lead filter as shown in the following equation (1):

$$\frac{s^2 + 2 \cdot z_1 \cdot w_1 \cdot s + w_1^2}{s^2 + 2 \cdot z_2 \cdot w_2 \cdot s + w_2^2} \quad (1)$$

where s represents Laplace operator, w1 and w2 represent frequencies to be set and they are in a relation of w1<w2, and z1 and z2 represent attenuation coefficients and they are in a relation of z1>z2. The filter characteristics are obtained by measuring transmission characteristics from a motor position command signal 154 generated by the adder 150 to positions of tip ends of the hauling wires 114 and 116, and by approximating its counter model. Therefore, an operation command signal basically passes through the feedforward control unit 152 as the command value signal 146, a transfer function to a later-described motor feedback closed loop system, and positions of the tip ends of the hauling wires 114 and 116 becomes substantially 1, and the bend position of the distal bending section 112 that is the tip positions of the hauling wires 114 and 116 moves substantially equally to the operation command value.

The adder 150 to which the feedforward control system is input is constructed as a position command value signal generation unit. The position command value signal generation unit corrects the feedforward control system by means of a feedback control system, and generates a motor position command signal 154 as a position command value signal to the motor 120. The motor position command signal 154 has been input to an adder 156. In addition to the motor position command signal 154, a motor position signal 160 has been input from a motor position detector 158. A signal indicative of a rotation angle has been input to the motor position detector 158 from a rotary encoder 162 that detects a rotation angle of the motor 120. The motor position detector 158 generates a motor position signal 160 in accordance with the rotation angle of the motor 120 detected by the rotary encoder 162. That is, the rotary encoder 162 and the motor position detector 158 are constructed as drive position detecting unit. The drive position detecting unit detects a position caused when the motor 120 is driven, and outputs the motor position signal 160 as the drive position detecting signal to the adder 156.

The adder 156 is constructed as a position deviation calculating unit that calculates a deviation between the motor position command signal 154 and the motor position signal 160. A signal concerning a position deviation calculated by the adder 156 has been input to a motor control unit 164. The motor control unit 164 is constructed as a calculation unit that includes a PID (proportion, integration, differentiation) and that carries out calculation for bringing a deviation generated by the adder 156 into zero, thereby generating a drive signal, and outputs the drive signal to a motor amplifier 166. The motor amplifier 166 amplifies the drive signal, and outputs the amplified drive signal to the motor 120.

In the above-described structure, if the operator operates the joystick 110, an operation command value corresponding to the operation is output as a command value signal 146, a deviation between the command value signal 146 and the wire tip end position signal 138 is calculated by the adder 142, a feedback control signal corresponding to the deviation is generated by the feedback control unit 148, feedforward compensation calculation for advancing the phase of the position command value signal 146 is carried out by the feedforward control unit 152, and a feedforward control signal is generated. The feedforward control signal is corrected by the feedback control signal, the motor position command signal 154 is generated, a position deviation corresponding to the deviation between the motor position command signal 154 and the motor position signal 160 is obtained by the adder 156, a drive signal based on the position deviation is generated by the motor control unit 164. If the motor 120 is normally or reversely rotated by the drive signal, the hauling wire 114 or 116 hauls, and the tip end of the distal bending section 112 is bent upward or downward. In this case, the motor 120 cancels a reaction force of the tensions of the hauling wires 114 and 116 applied to the pulley 118, and the rotation position of the motor 120 can follow the motor position command signal 154 substantially without delay. If a rattle of gear is ignored, a moving amount of wire near the pulley 118 that is moved by rotation of the pulley 118 can be calculated by multiplying the motor position command value signal 154 by a gear ratio and a radius of the pulley 118.

However, a moving amount of the hauling wire 114 or 116 in the vicinity of the pulley 118 that was moved by rotation of the pulley 118 and a moving amount of the hauling wire 114 or 116 on the side of the tip end of the distal bending section 112 are not proportional to each other. This may be because that tensions of the hauling wires 114 and 116 are attenuate by friction between the hauling wires 114 and 116 and the coil sheaths 122 and 124 in progress, a phase delays due to time blank (dead zone) that is elapsed before slack is taken up when the rotation of the pulley 118 is reversed, or dynamics act to prevent the distal bending section 112 comprising a hose and a tube from being bent.

In this embodiment, dynamics from the position of the pulley 118 where the phase delays to a position of the tip end of the correction table 12 are allowed to move using the feedforward control unit 152 that advances the phase of the command value signal 146, a following error that can not be compensated by this is compensated by a feedback control unit 146. Therefore, it is possible to allow the tip end position of the correction table 12 (bending position) to follow the operation command value without delay.

In the eighth embodiment, since the moving amounts of the hauling wires 114 and 116 are detected by the sensors 128 and 130, positions of the hauling wires 114 and 116 that are attenuated by friction or slack can be detected. By feeding back this detecting signal, it is possible to compensate nonlinearity caused by friction included in a system that constitutes the hauling unit or slack of the wire.

In this embodiment, a wire mechanism of the inserting portion is basically stable system, and an offset with respect to the operation command value may be adjusted by an operator by visually checking the monitor. Therefore, the feedback control unit 148 is not provided with integration characteristics or differentiation characteristics, and only gain compensation is carried out. By carrying out the feedback, gain is increased in a specific frequency band in some cases. Therefore, characteristics of a closed-loop are corrected using a notch filter if necessary.

When the gain of the feedback control unit 148 is increased, it follows the operation command value that is a target, but if the gain is excessively increased, since abrupt reverse operation of the motor is repeated to generate vibration, the feedback gain is set to one to two times. In this case, since the feedback gain is reduced, the operation command value and the tip end position of the distal bending section 112 do not coincide with each other completely, but by advancing the phase of the operation command value signal 146 using the feedforward control unit 152, it is possible to allow the tip end position of the distal bending section 112 to instantaneously follow the operation command value.

Figure 14A:
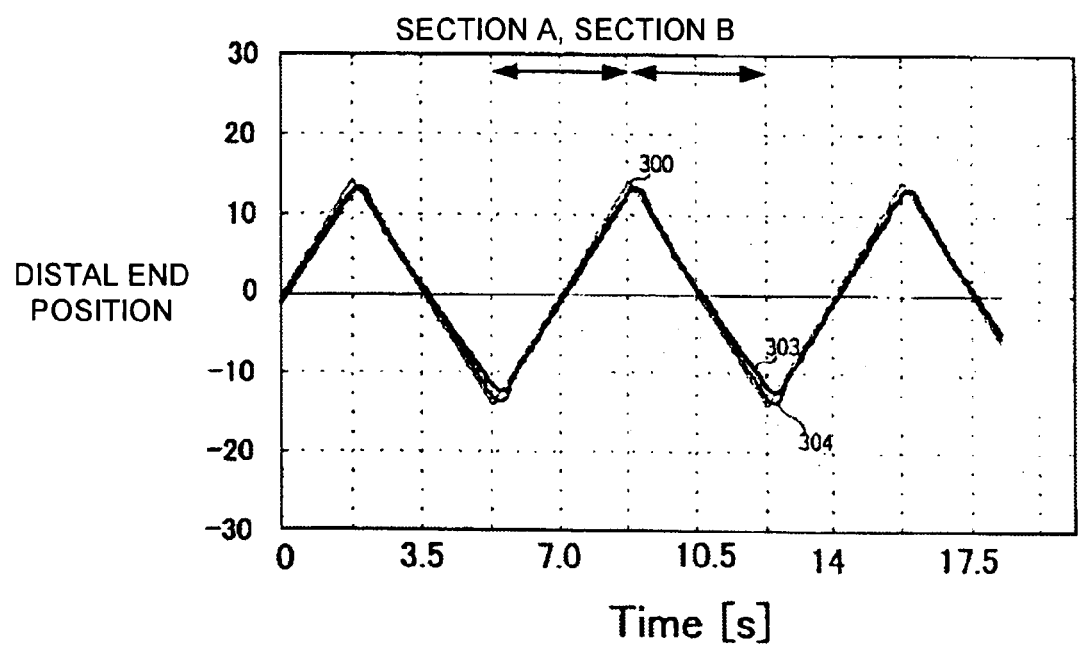
FIG. 14A and FIG. 14B are graphs of time-varying response waveforms of distal tip position and wire tension, respectively, according to the eighth embodiment.
Figure 14B:
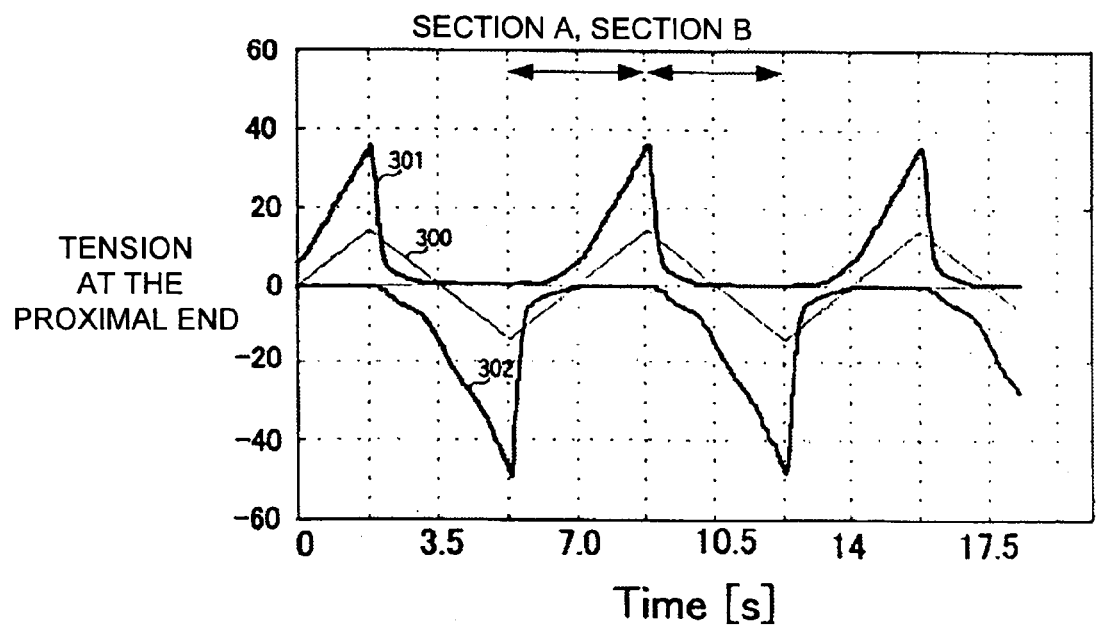
Figure 15A:
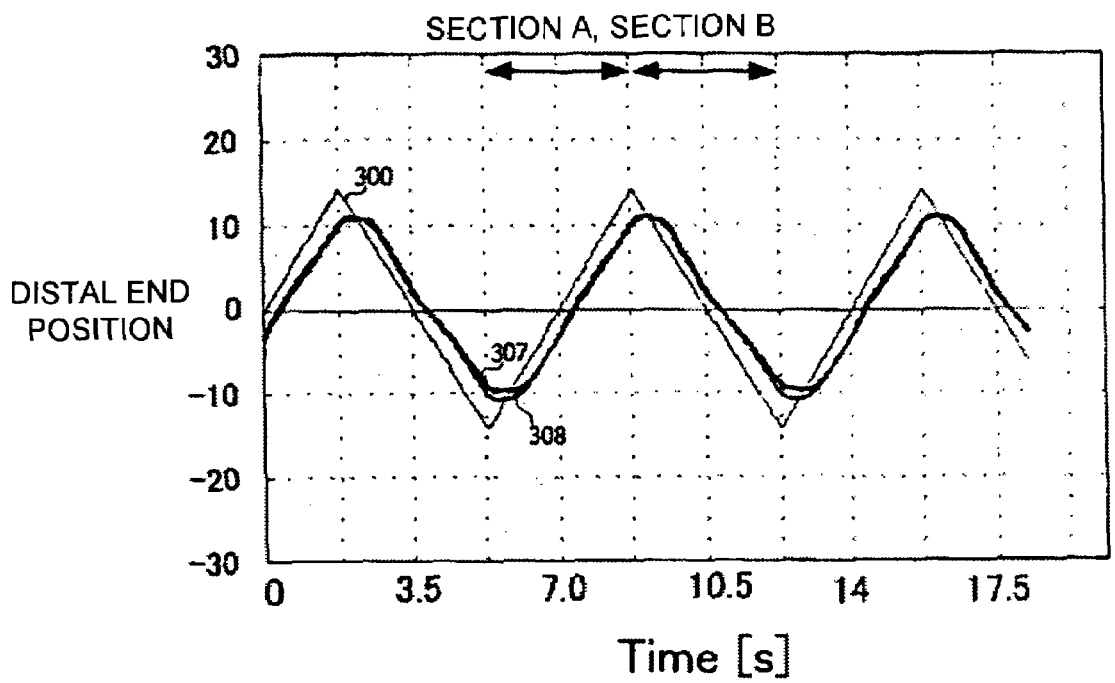
FIG. 15A and FIG. 15B are graphs of time-varying response waveforms of the distal tip position and the wire tension according to a conventional technology.
Figure 15B:
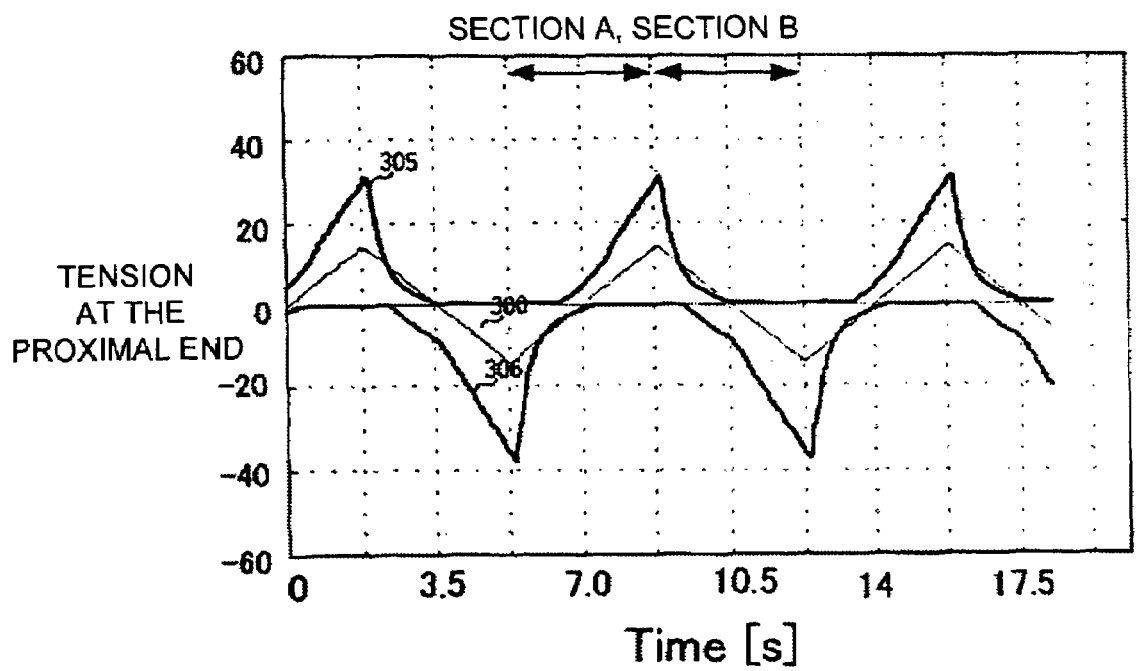

Results of experiments of the apparatus of the present invention and the conventional art will be explained with reference to FIGS. 14A, 14B, 15A and 15B. FIGS. 14A and 14B illustrate one example of the experiment result when a bending and positioning action of the endoscope is carried out by the control device. FIGS. 15A and 15B illustrate a response result by the conventional art in which a position command signal by operation of the joystick is directly generated as a motor position command signal. FIGS. 14A and 15A illustrate time waves in the tip end positions of the upper and lower hauling wires. FIGS. 14B and 15B illustrate time waves in which tensions applied to the upper and lower hauling wires of the endoscope inserting portion were measured on the side of the pulley. In each of the drawings, triangular waves having a period of seven seconds are shown. A command signal from the joystick is applied to a command signal 300. The pulley 118 illustrated in FIG. 13 is rotated in the direction of arrow (clockwise direction) in a section A, and is rotated in the counterclockwise direction in a section B.

In FIGS. 15A and 15B, it is found that in the conventional art, tip end positions 307 and 308 of the upper and lower wires have phases that delay with respect to a target command signal 300 by about 20 degrees, and gain is in a form of a triangle whose head becomes flat, i.e., in a form of a trapezoid. Therefore, in the conventional art, when an operator desires to allow the tip end of the distal bending section to follow the triangular wave and the operator only inputs a command signal of the triangular wave using the joystick, the phase of the tip end position of the distal bending section delays, and since the gain is in the form of trapezoid, the operator can not precisely position. Therefore, in order to achieve the object, the operator must correct the command signal by himself or herself while visually checking the monitor so that the tip end position of the distal bending section follows the triangular wave. For this reason, skill is required for operation, and since the motorized endoscope is used, a load to the operator is increased.

According to the present invention, as illustrated in FIGS. 14A and 14B, the tip end positions 303 and 304 of the upper and lower hauling wires and the target command signal (operation command signal) 300 substantially coincide with each other. Therefore, since the tip end positions of the hauling wires 114 and 116 move in accordance with a command signal, a load to the operator is reduced using the motorized endoscope, and it is possible to position the tip end of the distal bending section to a target location swiftly and precisely.

When tensions are compared with each other, if waveform of the conventional art illustrated in FIG. 15B is observed, a tension 305 at the instant when the rotation direction (operation direction) is changed from the section A to the section B is the greatest, and irrespective of the fact that the rotation direction is changed, the tension is gradually reduced, a tension 306 of the lower wire is zero. That is, irrespective of the fact that a state of slack is shifted to the section B and the rotation direction is changed, the tension starts increasing after about 0.7 seconds due to the slack, and the direction of the tip end position is changed.

On the other hand, according to the present invention, as illustrated in FIG. 14B, it is found that the tension 302 starts increasing substantially instantaneously from the section B. This is effect of the feedforward control unit 152 that advances the phase of the target command signal (operation command value) and the feedback control unit 148 that feedback controls the tip end position of the wire. Since the tensions of the hauling wires 114 and 116 are increased, the tip end positions of the hauling wires 114 and 116 can be controlled by the pulley 118. According to another conventional art that focuses on slack and tries to swiftly resolve the slack, the tip end position of the wire is largely deviated from the target command signal during that time. Therefore, an operator must try to coincide the tip end position of the wire to the command signal, a skill is required, and since a motorized endoscope is used, a load to the operator is increased.

A ninth embodiment of the present invention will be explained with reference to FIG. 16. In the ninth embodiment, the feedback control system for feedback controlling the tip end position of the hauling wire is removed from the control device illustrated in FIG. 13. Other structures of the ninth embodiment are the same as those in FIG. 13.

In the ninth embodiment, a phase of the command signal 146 by an output of the command signal detector 144 is advanced to generate a feedforward control signal, a deviation between the feedforward control signal and the motor position signal 160 is obtained by the adder 156, a drive signal for bringing this deviation to zero is generated by the motor control unit 164, this drive signal is amplified by the motor amplifier 166, and the motor 120 is rotated. The tip end position of the distal bending section 112 hauled by the hauling wires 114 and 116 can be allowed to follow the operation command value without delay. That is, in the process from the action of the pulley 118 to the tip end positions of the hauling wires 114 and 116, the phase delays due to influences of nonlinearity such as friction between the hauling wires 114 and 116 and the coil sheaths 122 and 124 and the slack of the hauling wires 114 and 116, but this phase delay can be compensated by the feedforward control unit 152. Therefore, if the phase of the operation command signal is advanced by the feedforward control unit 152, it is possible to advance the motion of the pulley 118 with respect to the operation command value.

Figure 17A:
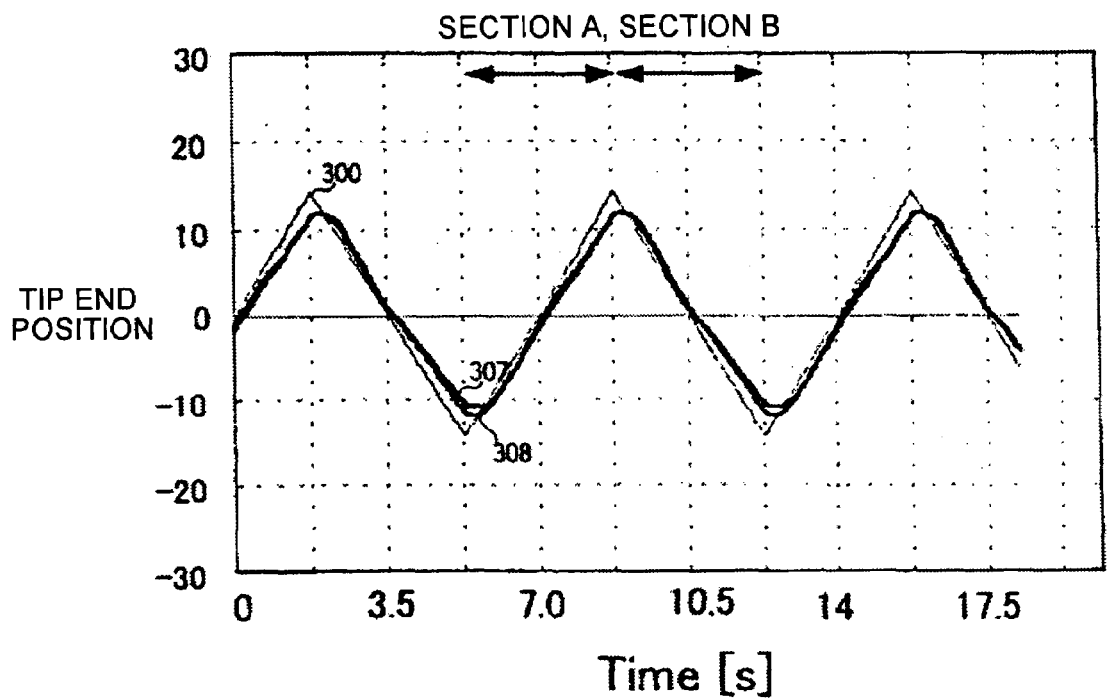
FIG. 17A and FIG. 17B are graphs of time-varying response waveforms of distal tip position and a command value, respectively, according to a ninth embodiment of the present invention.
Figure 17B:
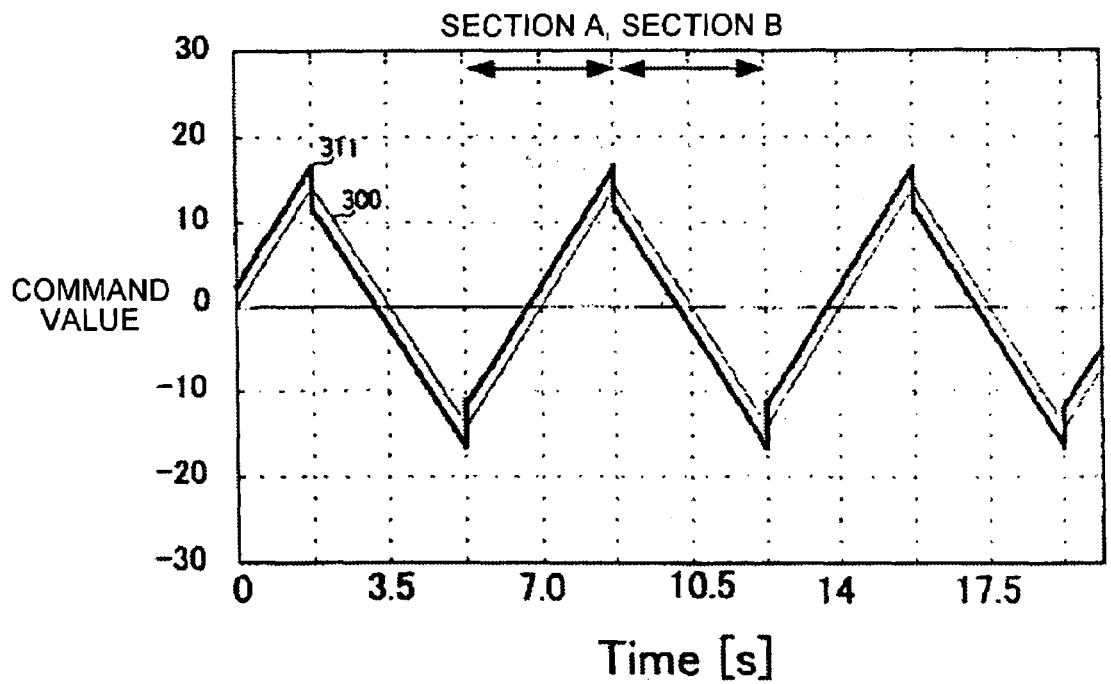
Figure 18:
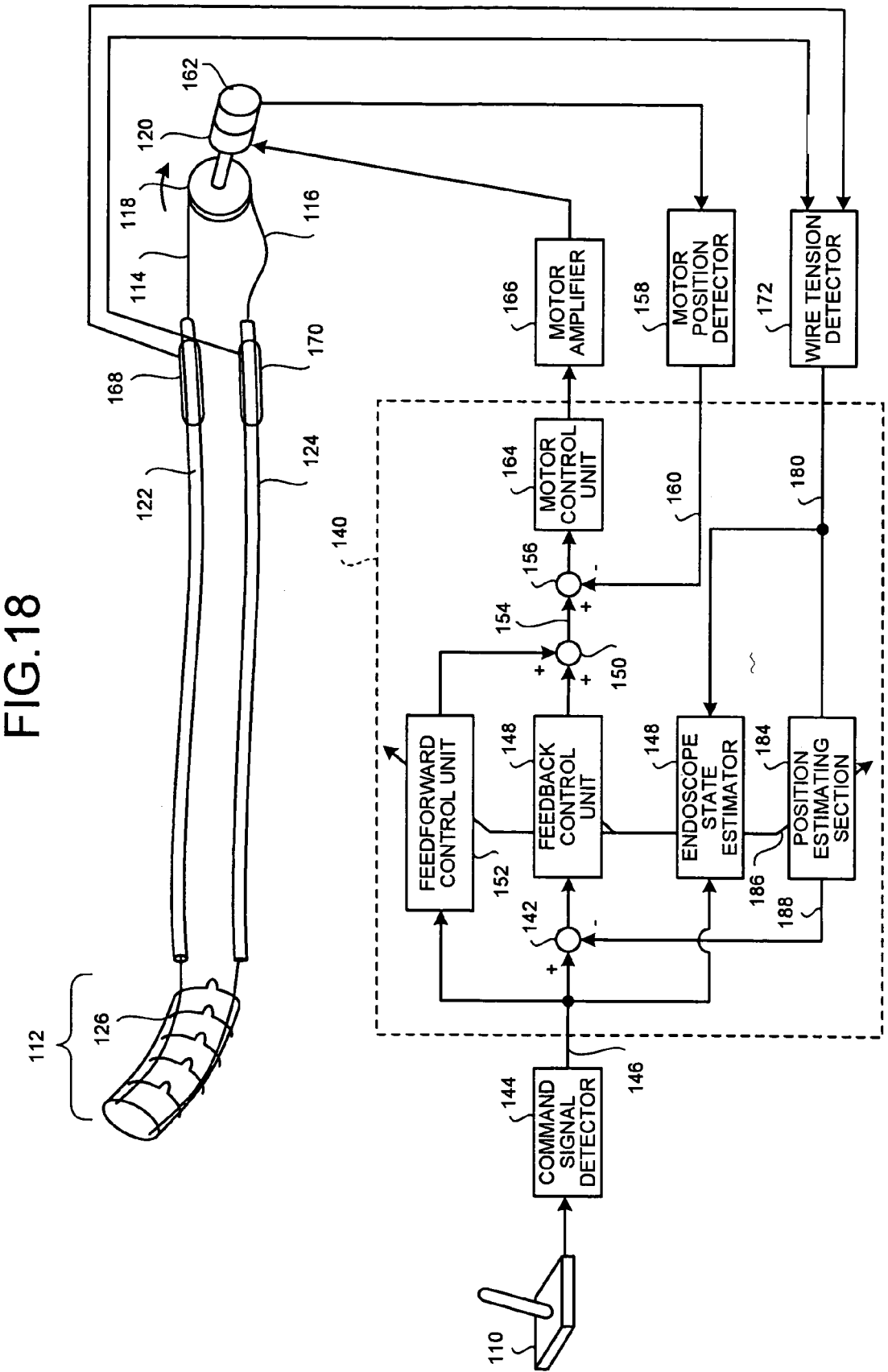
FIG. 18 is a schematic diagram of a motorized endoscope according to a tenth embodiment of the present invention.

In the ninth embodiment, a relation between the operation command signal and tip end positions of the hauling Wires 114 and 116 was measured, and experiment results as illustrated in FIGS. 17A and 17B were obtained. FIG. 17B illustrates characteristics of triangular wave 300 indicative of the operation command value and waveform 311 of a motor position command signal that is output from the feedforward control unit 152. It is found from FIGS. 17A and 17B that whenever the operation direction is changed by operating the joystick 110, an appropriate offset is added to a command, and the command signal is corrected in a direction in which its phase advances. From this, it is found that as compared with the tip end positions 307 and 308 illustrated in FIG. 15A, the tip end positions 307 and 308 of the hauling wires 114 and 116 in FIG. 17A approach the triangular wave 300 of the command signal.

It is found that, unlike the eighth embodiment, there is no feedback system in the ninth embodiment and motion of the tip end of the distal bending section 112 further approaches the operation command value by advancing the phase of the operation command value although it does not correspond to the characteristic variation such as friction of the inserting portion.

As the feedforward control unit 152 in the ninth embodiment, a structure in which a symbol is changed may be used as shown in the following equation (2):

$$g \cdot \text{sgn}(\dot{R}) \qquad (2)$$

where R represents a target command signal, and sgn represents its symbol. It is preferable that when speed of the command signal is smaller than a constant value, the magnitude of the gain g is proportional to the speed, and when the speed of the command signal becomes equal to or greater than the constant value, the magnitude of the gain g is equal to the constant value. With this, the speed of the motor 20 can gradually be varied with respect to the change of symbol of the speed and vibration of the wire 114 and 116 can be suppressed.

In the ninth embodiment, since the endoscope inserting portion is not provided with special sensors 128, 130 or the feedback control system, costs can be reduced as compared with the eighth embodiment.

A tenth embodiment of the present invention will be explained with reference to FIG. 18 to FIG. 23. In the tenth embodiment, tensions of the hauling wires 114 and 116 are detected instead of feeding back the tip end positions of the hauling wires, and the tensions are fed back. Tension sensors 168 and 170 for detecting the tensions of the hauling wires 114 and 116 are provided on the side of the pulley 118 of the hauling wires 114 and 116, and detection values of the tension sensors 168 and 170 are input to a wire tension detector 172.

Figure 19:
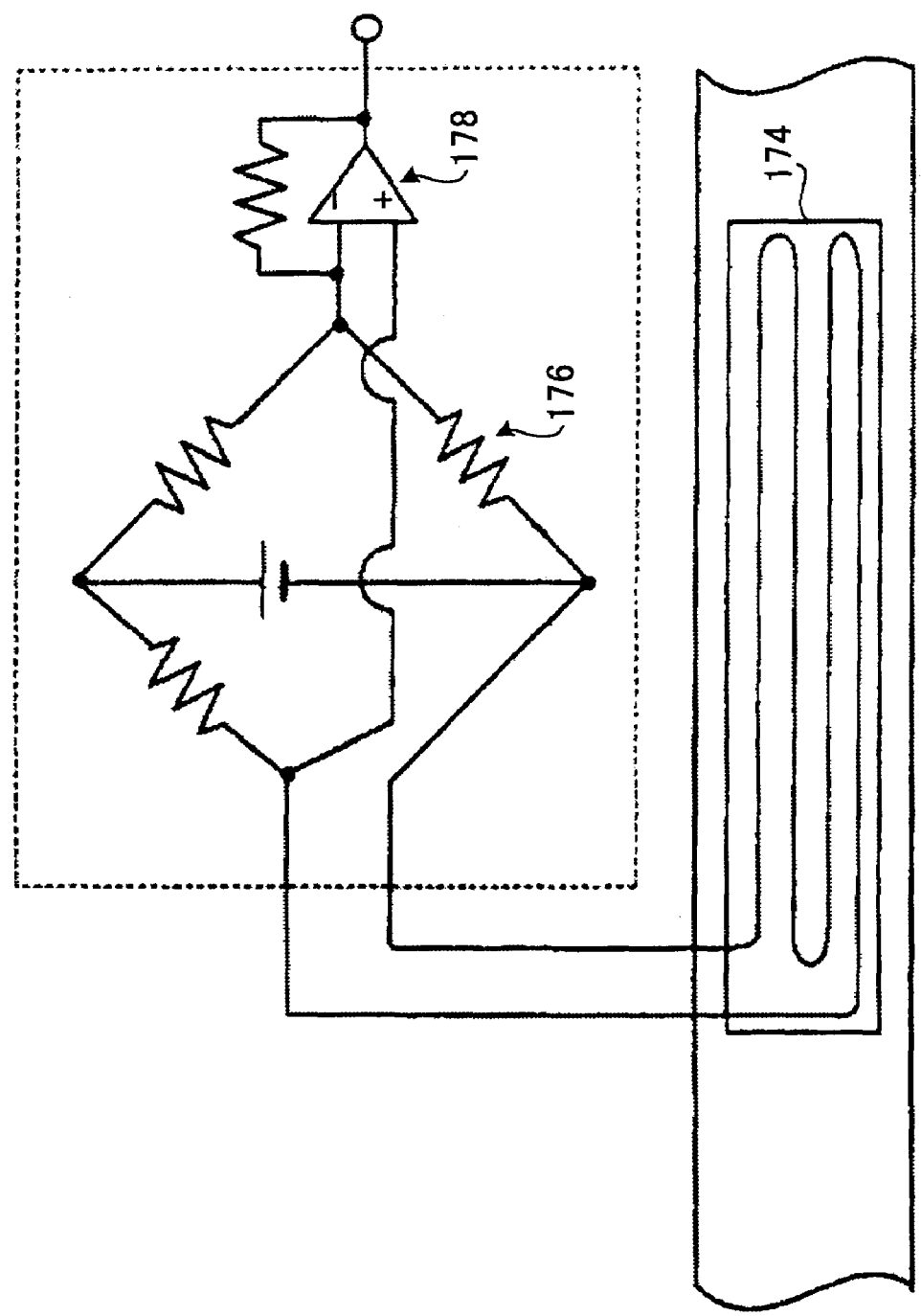
FIG. 19 is a circuit diagram of a wire tension detector.

As illustrated in FIG. 19, each tension sensor 168, 170 include a distortion gage 174, a bridge circuit 176 and a differential amplifier circuit 178. A fine thin and long distortion gage 174 is mounted to each of the hauling wires 114 and 116. If variation in distortion amount is detected by the distortion gage 174, a signal indicative of the variation of distortion amount is amplified by the differential amplifier circuit 178 through the bridge circuit 176 that varies a resistance in proportion to the variation of the distortion amount. In this case, when no external force is applied to the hauling wires 114 and 116, balance of the bridge circuit 176 is kept by a resistance of the distortion gage 174, and an output of the differential amplifier circuit 178 is zero. On the other hand, if the hauling wire 114 or 116 is pulled by the pulley 118, an external force is applied to the hauling wire 114 or 116, a resistance of the distortion gage 174 is changed, balance of the distortion gage 174 is lost, and voltage is generated in the output end of the differential amplifier circuit 178. This output voltage is output to the wire tension detector 172 as a signal indicative of tension that is applied to the hauling wire 114 or 116. The wire tension detector 172 adds tensions detected by the tension sensors 168 and 170, and outputs an internal tension signal 180 indicative of a substantial internal tension that pulls the tip end of the distal bending section 112. That is, the tension sensors 168 and 170 and the wire tension detector 172 are constructed as tension detecting units, and the internal tension signal 180 is output to an endoscope state estimator 182 and a position estimator 184. Positive and negative of tensions detected by the tension sensors 168 and 170 have the same relation as the characteristics illustrated in FIG. 14B.

The position estimator 184 is constructed as a position estimating unit. The position estimating unit estimates a bend position of the distal bending section 112 from an internal tension signal 180 and an estimated result 186 of the endoscope state estimator 182, and outputs this estimated result 188 to the adder 142 as a hauling property detecting signal. The position estimator 184 is constructed by modeling dynamics from the internal tension signal 180 to the tip end positions of the hauling wires 114 and 116. By selecting a designated model from a plurality of models in accordance with the state estimated result 186, the tip end position of the inserting portion can be estimated. The model used for the position estimator 184 is constituted by using a plurality of primary low pass filters. When the model is selected from the state estimated result 186, it is necessary to select a designated model in accordance with a state of the inserting portion of the endoscope. That is, since the inserting portion is inserted into a body cavity or the like, the inserting portion is substantially in a straight state at an initial stage of insertion, but when the inserting portion is inserted along a shape of a bowel or the like, a bending ratio of an intermediate portion of the inserting portion becomes great depending upon a location in some cases. If the bending ratio is increased, friction between the coil sheaths 122 and 124 and the hauling wires 114 and 116 is increased, characteristics of dynamics from the measured internal tension signal 180 to the tip end positions of the hauling wires 114 and 116 are varied as compared with those when the inserting portion is straight. Further, the characteristics of dynamics are also varied by a using environment state of the endoscope or variation with time. Therefore, in order to further enhancing the estimation precision of the tip end position (bend position) of the hauling wire, it is necessary to estimate these states, to select a model corresponding to this estimation, and to control the feedback control unit 148 in accordance with the selected model.

Hence, in the tenth embodiment, in the endoscope state estimator 182, the state estimated result 186 for selecting an appropriate model is obtained in accordance with a function that is previously determined from a relation ratio between the command signal 146 indicative of the operation command value and the internal tension signal 180 indicative of a magnitude of the internal tension, and the state estimated result 186 is output to the position estimator 184. The state estimated result 186 is obtained while taking into account the fact that characteristics variation of dynamics from the internal tension signal 180 to the tip end positions of the hauling wires 114 and 116 appear most remarkably in tension. That is, even if the operation command values are the same, when the motor 120 is driven based on the operation command value, if the inserting portion is straight, tension applied to the hauling wires 114 and 116 is small, and if the bending ratio of the inserting portion is great and an intermediate portion of the inserting portion is rotated, tension applied to the hauling wires 114 and 116 is great. For this reason, the endoscope state estimator 182 estimates the state of the distal bending section 112 from the operation command value and the internal tension, and the endoscope state estimator 182 is constructed as a state estimating unit that estimates the state of the distal bending section 112 from the operation command value signal 146 and the internal tension signal 180.

Figure 20A:
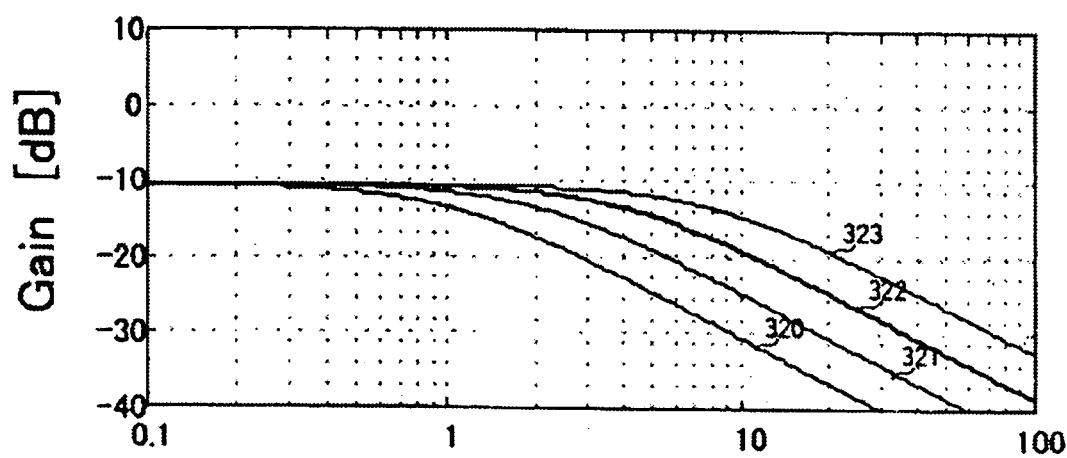
FIG. 20A and FIG. 20B are graphs of characteristics of a model used for a position estimator.
Figure 20B:
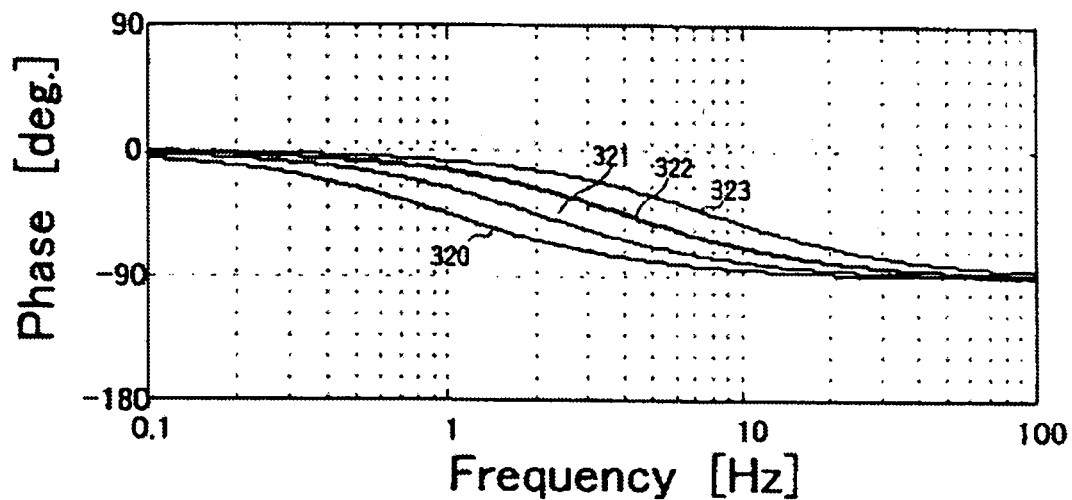

As a model used for the position estimator 184, it is possible to use four primary low pass filters as illustrated in FIGS. 20A and 20B. Characteristics of the four models are indicated with 320, 321, 322 and 323, and crossover frequencies of the characteristics are 1 hertz, 2 hertz, 4 hertz, and 8 hertz, respectively. When the inserting portion is straight, characteristics 322 having crossover frequency of 4 hertz is used. When the intermediate portion of the inserting portion is rotated and its friction is great, characteristics 320 having crossover frequency of 1 hertz is used for example. The tip end position of a wire using the low pass filter having crossover frequency of 4 hertz was estimated as a model, experiment results as illustrated in FIG. 21 were obtained. In this case, although a trapezoidal waveform indicative of a position of the wire tip end did not completely coincide with the command signal, the phase characteristics coincided with the command signal, and it could be confirmed that the tip end positions 307 and 308 of the hauling wires coincided with a result 312 estimated by the position estimator 184.

Figure 22:
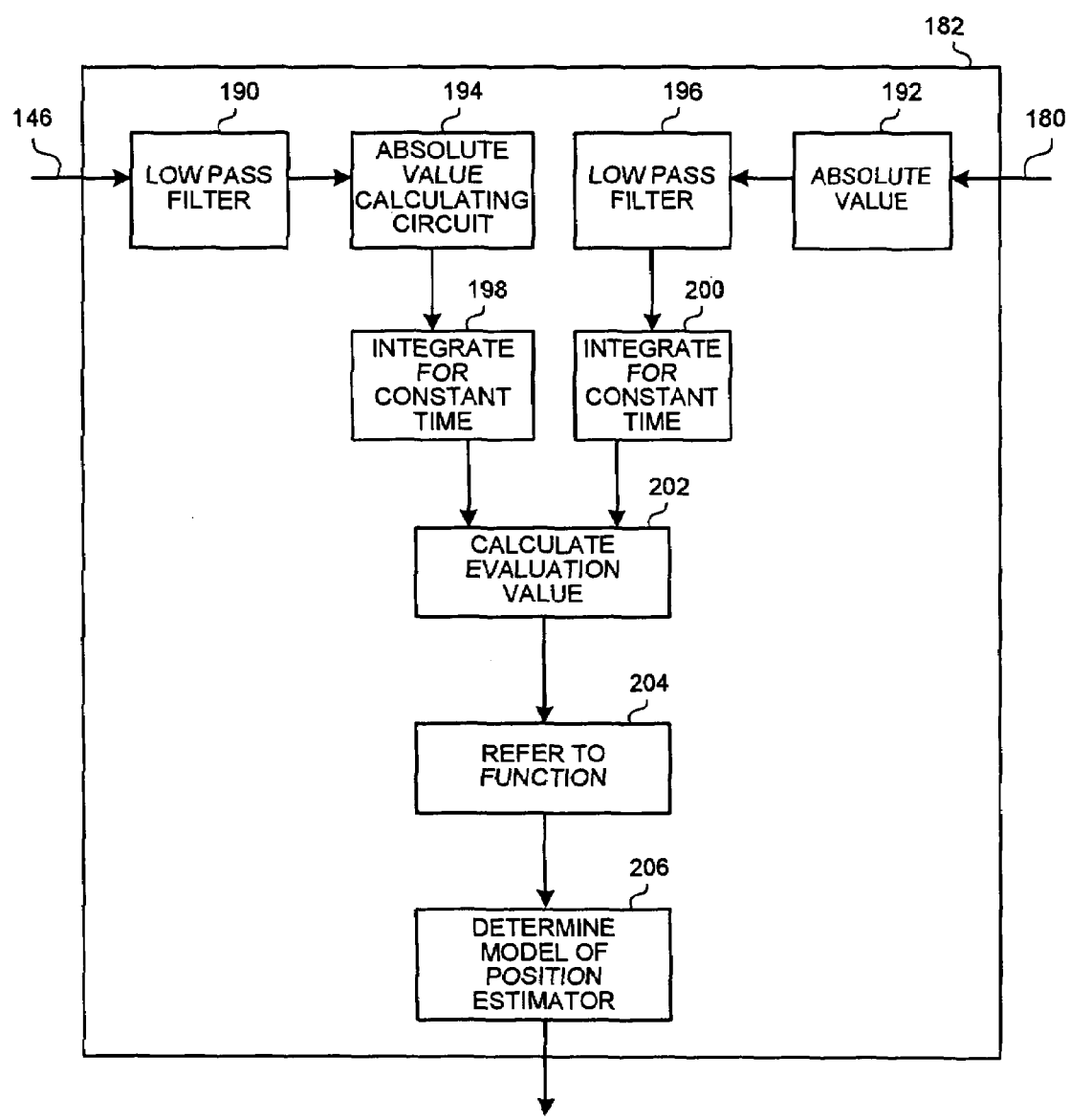
FIG. 22 is a block diagram of an endoscope state estimator.

As illustrated in FIG. 22, the endoscope state estimator 182 comprises low pass filters 190 and 192, absolute value calculating circuits 194 and 196, integration circuits 198 and 200, an evaluation value calculating circuit 202, a function reference circuit 204 and a model determining circuit 206. A command signal 146 based on the operation of the joystick 110 has been input to the low pass filter 190, and since the command signal 146 passes through the low pass filter 190, noise component is cut off and only signals of necessary band pass. A signal that passed through the low pass filter 190 is converted into a positive signal by the absolute value calculating circuit 194, the signal is integrated by constant time T0, and the integrated value is output to the evaluation value calculating circuit 202 as an operation command signal having magnitude of RI. In this case, if the operation command value is defined as R, RI is obtained by the following equation (3):

$$RI = \int_0^{T0} |R| dt \qquad (3)$$

An internal tension signal 180 has been input to a low pass filter 192, noise component of the internal tension signal 180 is removed by the low pass filter 192, and only signals having necessary band pass through the low pass filter 192, and a signal that passed through the low pass filter 192 is converted into a positive signal by the absolute value calculating circuit 196. If the signal is integrated by constant time T0 by an integration circuit 200, the integrated value is output to the evaluation value calculating circuit 202 as a signal indicative of an internal tension C having magnitude of CI. In this case, the magnitude CI of the internal tension C is obtained by the following equation (4):

$$CI = \int_0^{T0} |C| dt \qquad (4)$$

Figure 23:
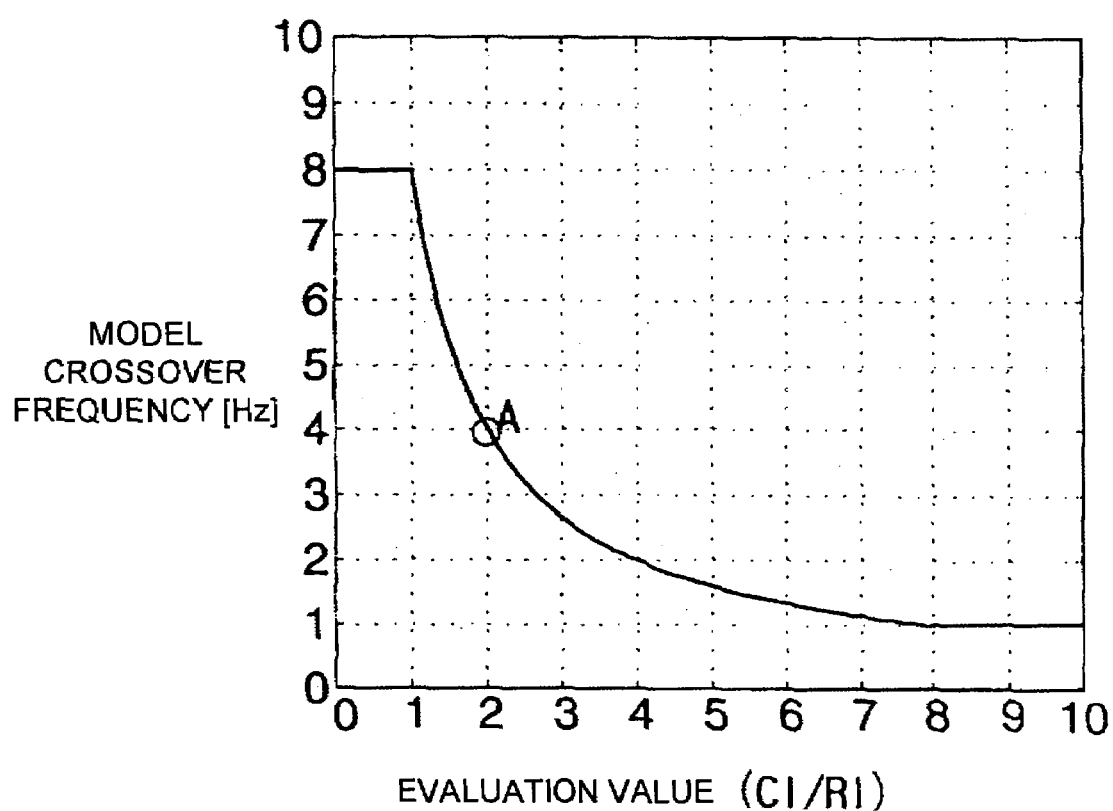
FIG. 23 is a graph of a relation between an evaluation value and a model used for an endoscope state estimator.

By dividing the magnitude RI of the operation command value by the magnitude CI of the internal tension in the evaluation value calculating circuit 202, an evaluation value concerning a state of the endoscope inserting portion is calculated. When making a reference to a function in the function reference circuit 204 in accordance with this evaluation value, a relation between an evaluation value and a model crossover frequency as illustrated in FIG. 23 is set. This relation is expressed as shown in the following equation (5):

$$\frac{8}{CI/RI} \qquad (5)$$

If a model crossover frequency corresponding to the evaluation value is determined, a model of the model crossover frequency corresponding to the evaluation value is determined by the model determining circuit 206, and this determination is output as a state estimated result 186.

When the evaluation value is greater than 8, for example, i.e., when the tension is greater with respect to an operation command signal, this unit that delay of dynamics of the inserting portion becomes great due to friction or the like, and a low pass filter having crossover frequency of 1 hertz is selected as a model. When the evaluation value is between 1 and 8, a model crossover frequency is calculated in accordance with the equation (5), and when the evaluation value is smaller than 1, model crossover frequency is set to 8 hertz. For example, when the evaluation value is 2 and an intersection point with respect to a function is A, the evaluation value is straight, and crossover frequency of 4 hertz is selected as a model at that time.

Instead of integrating a signal that passed through the absolute value calculating circuit 194, 196 for predetermined time, it is also possible to use a signal that passed through a low pass filter of about zero. 1 hertz for predetermined time. The model may be renewed every constant time.

In the tenth embodiment as described above, since the estimated result 188 estimated by the position estimator 184 is fed back and the feedback control is carried out, a following error that can not be completely compensated by the feedforward control unit 152 can be compensated by the feedback control system.

In the tenth embodiment, since the model is renewed in accordance with a state of the endoscope inserting portion every constant time in the feedforward control unit 152 and the feedback control unit 148, it is possible to position with higher precision.

In the tenth embodiment, it is possible to renew a model and to adjust a parameter of the feedback control unit 148 and a parameter of the feedforward control unit 152.

Figure 24:
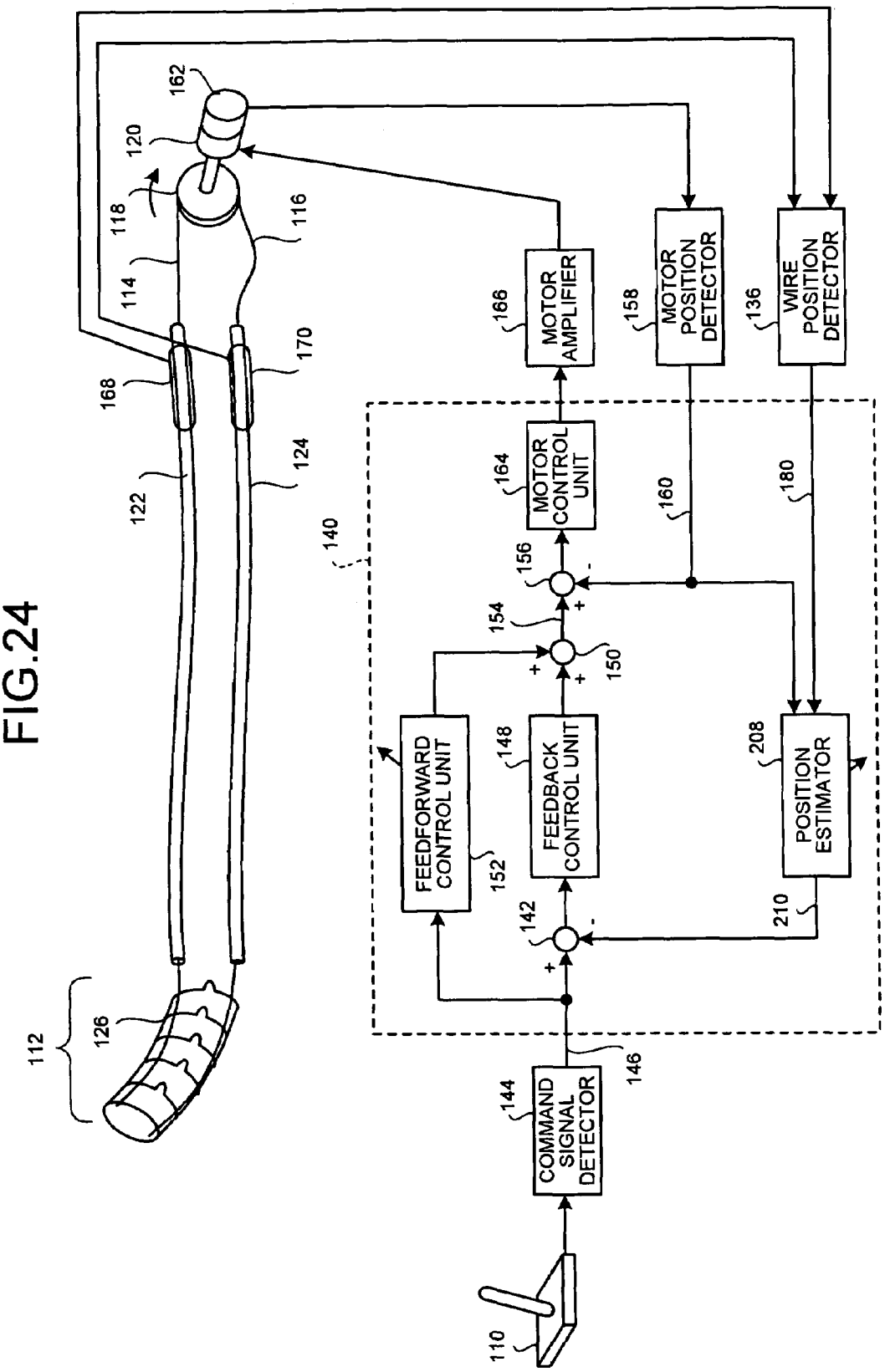
FIG. 24 a schematic diagram of a motorized endoscope according to an eleventh embodiment of the present invention.

An eleventh embodiment of the present invention will be explained with reference to FIG. 24. The eleventh embodiment comprises a position estimator 208 that estimates tip end positions of the hauling wires 114 and 116 from a motor position signal 160 indicative of a rotation movement amount of the pulley 118 and from an internal tension signal 180, instead of using the endoscope state estimator 182 and the position estimator 184 illustrated in FIG. 18. Other structures of the eleventh embodiment are the same as those illustrated in FIG. 18. The position estimator 208 is constructed as a position estimating unit. The position estimating unit receives a motor position signal 160 detected by the motor position detector 158 and an internal tension signal 180 detected by the wire tension detector 172. The position estimating unit estimates tip end positions (bend position of the distal bending section 112) of the hauling wires 114 and 116 based on these signals, and outputs the estimated result 210 to the adder 142 as a hauling property detecting signal.

In the position estimator 208, when the tip end positions of the hauling wires 114 and 116 are estimated from a motor position signal 160 corresponding to the rotation movement amount of the pulley 118 and an internal tension signal 180 indicative of the internal tension, assuming that rigidity of the hauling wires 114 and 116 is already known, the tip end positions of the hauling wires are estimated. In this case, it is considered that the internal tension Ten is generated in accordance with the following equation (6):

$$\text{Ten} = K \times (\text{Posp} - \text{Posf}) \tag{6}$$

where K represents rigidity of the hauling wire 114, 116, Posp represents a moving amount of hauling wire 114, 116 moved because the pulley 118 rotates, and Posf represents a tip end position of the hauling wire. To obtain the tip end position of the hauling wire, the equation (6) can be deformed into the following equation (7):

$$\text{Posf} = \text{Posp} - \text{Ten}/K \tag{7}$$

In the equation (7), if the rigidity of the hauling wires 114 and 116 is previously measured, the moving amount of wire of the Posp can be obtained by multiplying a gear ratio by a radius of the pulley 118 from a detection value of the rotary encoder 162. With this, the tip end positions of the hauling wires can be estimated in real time.

In the eleventh embodiment, since feedback control is carried out in accordance with a deviation between the estimated result 210 of position and the operation command value, it is possible to allow the tip end positions of the hauling wires to follow the operation command value.

Figure 25:
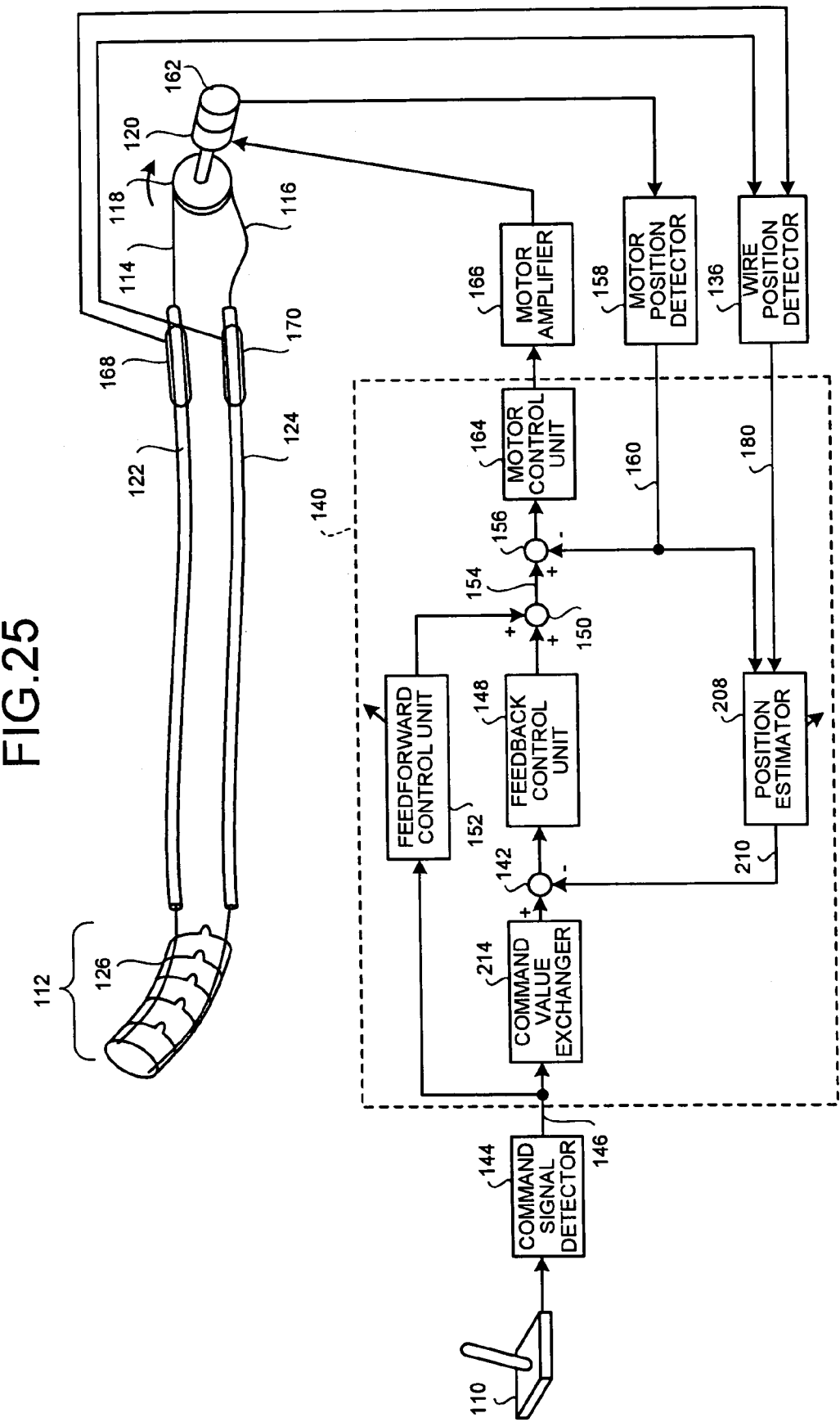
FIG. 25 is a schematic diagram of a motorized endoscope according to a twelfth embodiment of the present invention.

A twelfth embodiment of the present invention will be explained with reference to FIG. 25. In the twelfth embodi-
ment, taking into the consideration the fact that an operation command value obtained by operating the joystick 110 is a function of a position, a command signal 146 is converted into a tension command signal 214 in a command signal converter 212, a deviation between the tension command signal 214 and the internal tension signal 180 is obtained by the adder 142, and this deviation is fed back controlled by the feedback control unit 148. Other structures of the twelfth embodiment are the same as those illustrated in FIG. 16.

The command signal converter 212 is constructed as a command signal converting unit that includes a primary high pass filter for example. The command signal converting unit converts the command signal 146 into the tension command signal 214.

In the twelfth embodiment, since a deviation between the internal tension signal 180 and the tension command signal (tension command value signal) 214 is feedback controlled, the tip end positions of the hauling wires 114 and 116 can be allowed to follow the tension command signal.

When a tension command can be input directly to an input unit such as the joystick 110, a deviation between the signal and the internal tension may be input to the feedback control unit 148.

Figure 26:
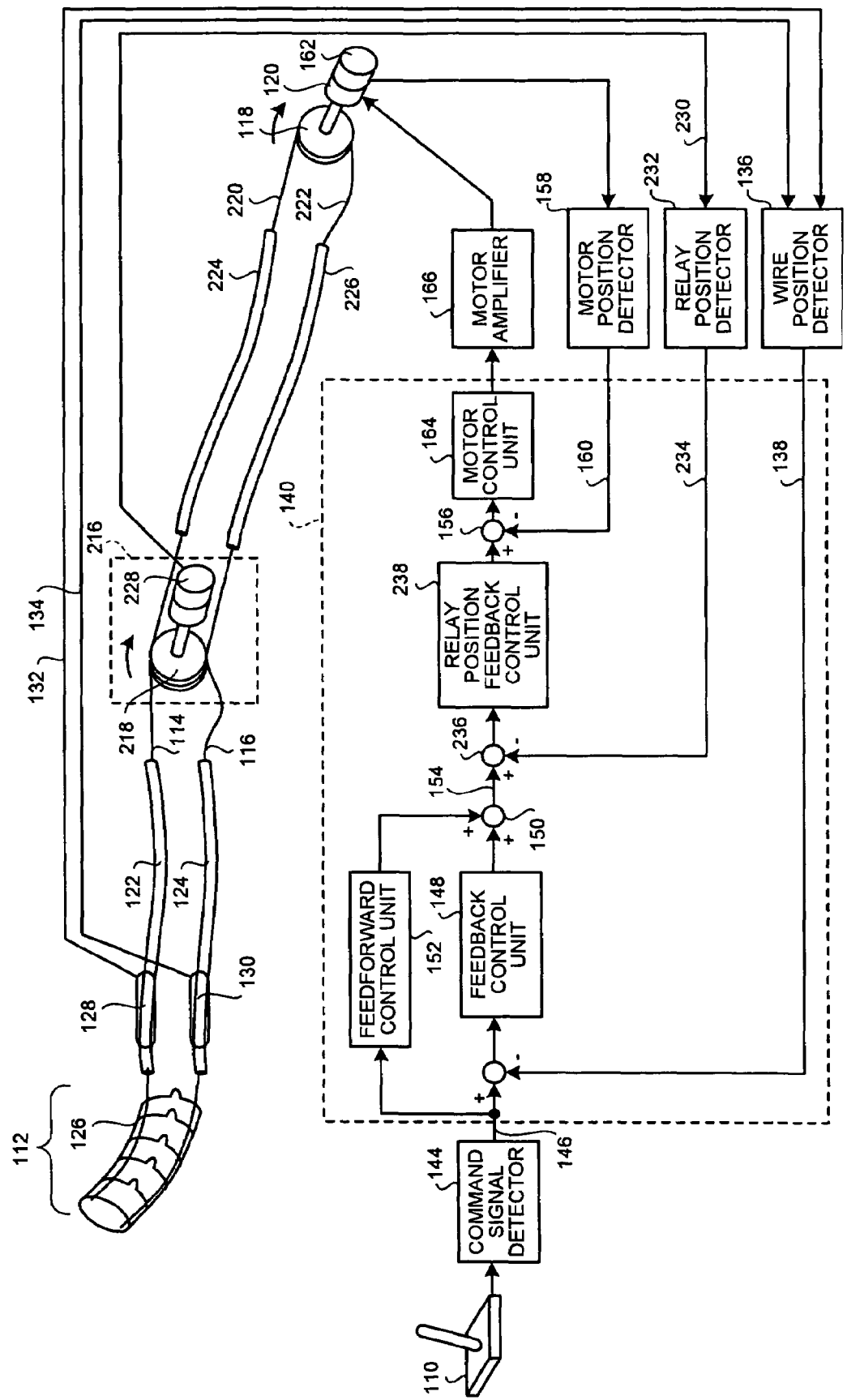
FIG. 26 is a schematic diagram of a motorized endoscope according to a thirteenth embodiment of the present invention.

A thirteenth embodiment of the present invention will be explained with reference to FIG. 26. In the thirteenth embodiment, the hauling wires 114 and 116 illustrated in FIG. 13 are wound around a relay pulley 218 provided in an operation section 216, one ends of hauling wires 220 and 222 are wound around the relay pulley 218 and inserted into coil sheaths 224 and 226, and the other ends of the hauling wires 220 and 222 are wound around the pulley 218, and the hauling wires 114 and 116 and the hauling wires 220 and 222 are connected to each other through the relay pulley 218, thereby constituting a plurality of hauling units. The relay pulley 218 is provided with a potentiometer 228 for detecting a rotation angle of the relay pulley 218. A rotation angle signal 230 detected by the potentiometer 228 is output to the relay position detector 232. That is, in the thirteenth embodiment, by providing the operation section 216 at an intermediate portion of the inserting portion through the relay pulley 218, a length of the inserting portion is shortened. The hauling wires 220 and 222 and the coil sheaths 224 and 226 located from the motor 120 to the relay pulley 218 are disposed in a universal cord in which an electrographic system such as CCD mounted to the tip end distal bending section 126. An operator can operate, using his or her thumb or the like, an input unit (not illustrated) such as the joystick 110 mounted to the operation section 216 that covers the relay pulley 218.

The relay position detector 232 outputs a relay position signal 234 indicative of a rotation angle of the relay pulley 218 to the adder 236 based on a rotation angle signal 230. That is, the potentiometer 228 and the relay position detector 232 are constructed as relay position detecting units that detect a position where a relay hauling unit of the hauling units drives, and output a relay position signal 234. The adder 236 receives a motor position command value signal 154 output from the adder 150 as a relay pulley position command signal, obtains a deviation between the relay pulley position command signal and the relay position signal 234, and outputs the deviation to the relay position feedback control unit 238. The relay position feedback control unit 238 generates a relay position feedback control signal for suppressing the deviation calculated by the adder 236 to zero, and outputs the relay position feedback control signal to the adder 156 as a motor position command signal. The adder 156 obtains a deviation between the motor position command signal and the motor position signal 160, and a drive signal corresponding to the deviation is generated by the motor control unit 164, and the drive signal is amplified by the motor amplifier 166 to drive the motor 120. That is, in the motor control unit 164, reaction of a tension applied to the pulley 118 is canceled, and the rotation angle of the motor 120 is allowed to follow the motor position command signal.

On the other hand, in the relay position feedback control unit 238, influence such as slack generated in an end of the pulley 118 connected to the motor 120 and friction of the hauling wires 220 and 222 in the universal cord is canceled, and the rotation angle of the relay pulley 218 is allowed to follow the relay pulley position command signal 154.

In the feedback control unit 148, influence of slack and friction existing in a portion from the relay pulley 218 to the tip end endoscope inserting portion is canceled, and the hauling wire tip end position is allowed to follow the operation command value.

Further, in the feedforward control unit 152, the phase of the operation command value is advanced, and dynamics from a position of the pulley where the phase delays to the tip end position of the wire are moved.

In the thirteenth embodiment, if the potentiometer 228 or the like is mounted to the relay pulley 218, the operation section 216 is increased in size and weight. Therefore, when the rotation angle of the relay pulley 218 can not be detected, the feedback of the motor position and the feedback of the wire position may be carried out. When the sensors 128 and 130 can not be mounted, the motor position command signal may be generated only by the feedforward control unit 152 comprising a phase leading filter. A tension sensor may be mounted to the inserting portion, and a tip end position of the wire may be estimated from a tension detected by the tension sensor. A tension sensor may be mounted to the hauling wire closer to the motor, and a position of the hauling wire may be estimated and the feedback may be carried out.

Since the thirteenth embodiment basically comprises a combination of two endoscope inserting portions, a plurality of hauling units may be provided also in the eighth embodiment to the twelfth embodiment. Further, one more relay pulley 218 may be added.

Although the distal bending section 112 of the motorized endoscope is operated in each of the embodiments, another apparatus that operates a tip end by hauling the tip end using a hauling wire or the like, e.g., an apparatus opens and closes an opening using a wire such as a wire-driving robot arm (hand) or forceps may be operated.

Although the feedforward control unit and feedforward control unit are used in the embodiment, even if one of them is provided, the same effect can be achieved.

In each of the embodiments, the control device comprises an analogue circuit, but the control device can also be controlled digitally using a microcomputer or the like.

According to each of the embodiments, it is possible to enhance the response of bending operation of the distal bending section 112 that is bent by hauling the same using the hauling wire by means of the motor 120 and the operation command value caused by operating the joystick 10, and to enhance the operability of positioning operation of the motorized endoscope.

According to the eighth embodiment to the thirteenth embodiment as explained above, since the operation command value is compensated by the feedforward control unit, the bend position that is to be operated can follow the operation command signal instantaneously, and this can enhance the operability.

In a fourteenth embodiment of the present invention, the first embodiment to the seventh embodiment, and the eighth embodiment to the thirteenth embodiment are appropriately combined.

Figure 27:
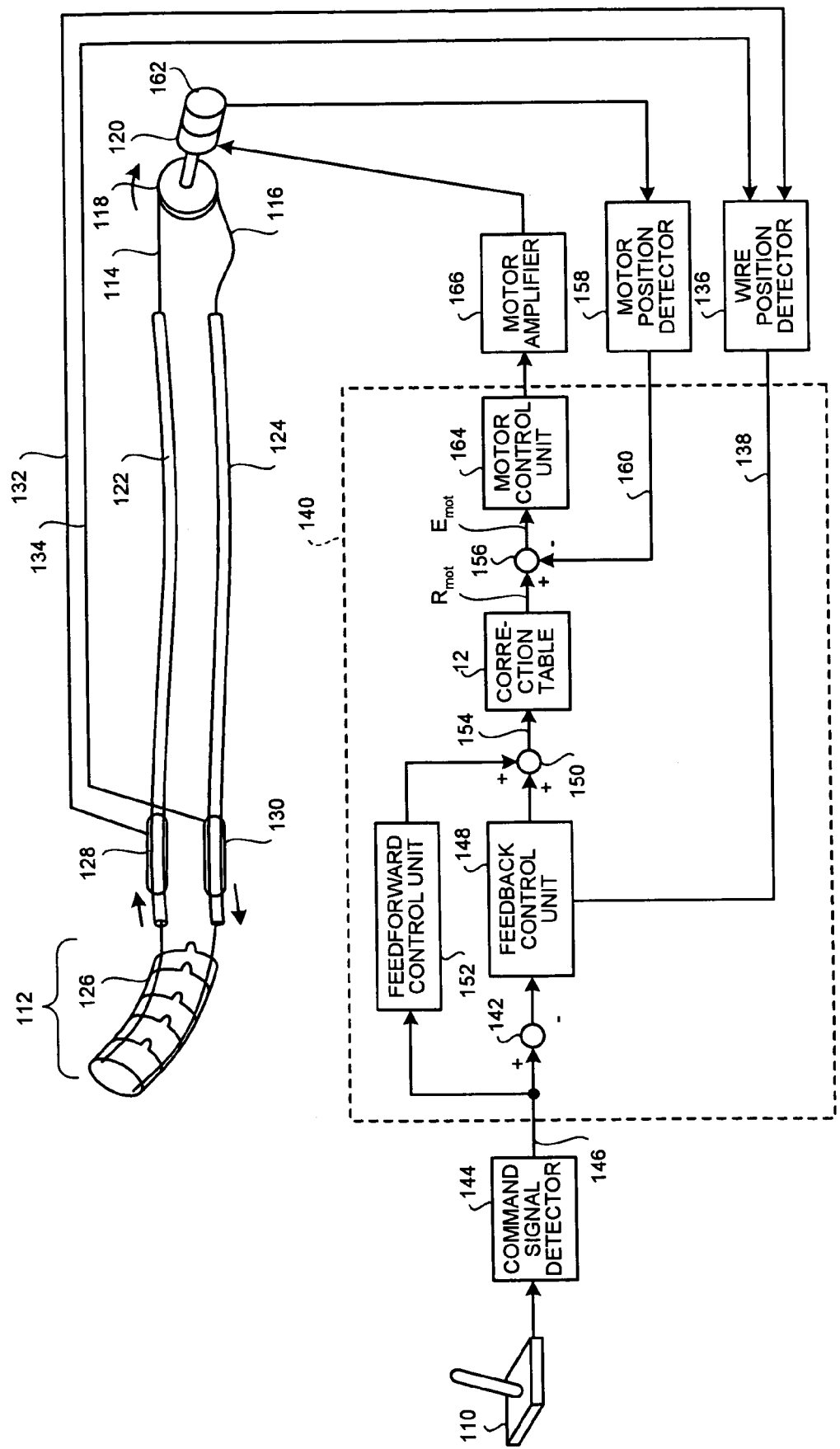
FIG. 27 is a schematic diagram of a motorized endoscope according to a fourteenth embodiment of the present invention.

For example, FIG. 27 illustrates a structure of the motorized endoscope in which the structure illustrated in FIG. 1 is applied to the structure illustrated in FIG. 13. In an motorized endoscope illustrated in FIG. 27, the control device 11 illustrated in FIG. 1 from which the motor control unit 13 is removed is provided in front of the motor control unit 164 illustrated in FIG. 27. With this structure, the motorized endoscope of the fourteenth embodiment exhibits the effect of the motorized endoscope of the eighth embodiment illustrated in FIG. 13, and exhibits the effect of the motorized endoscope of the first embodiment illustrated in FIG. 1.

Figure 28:
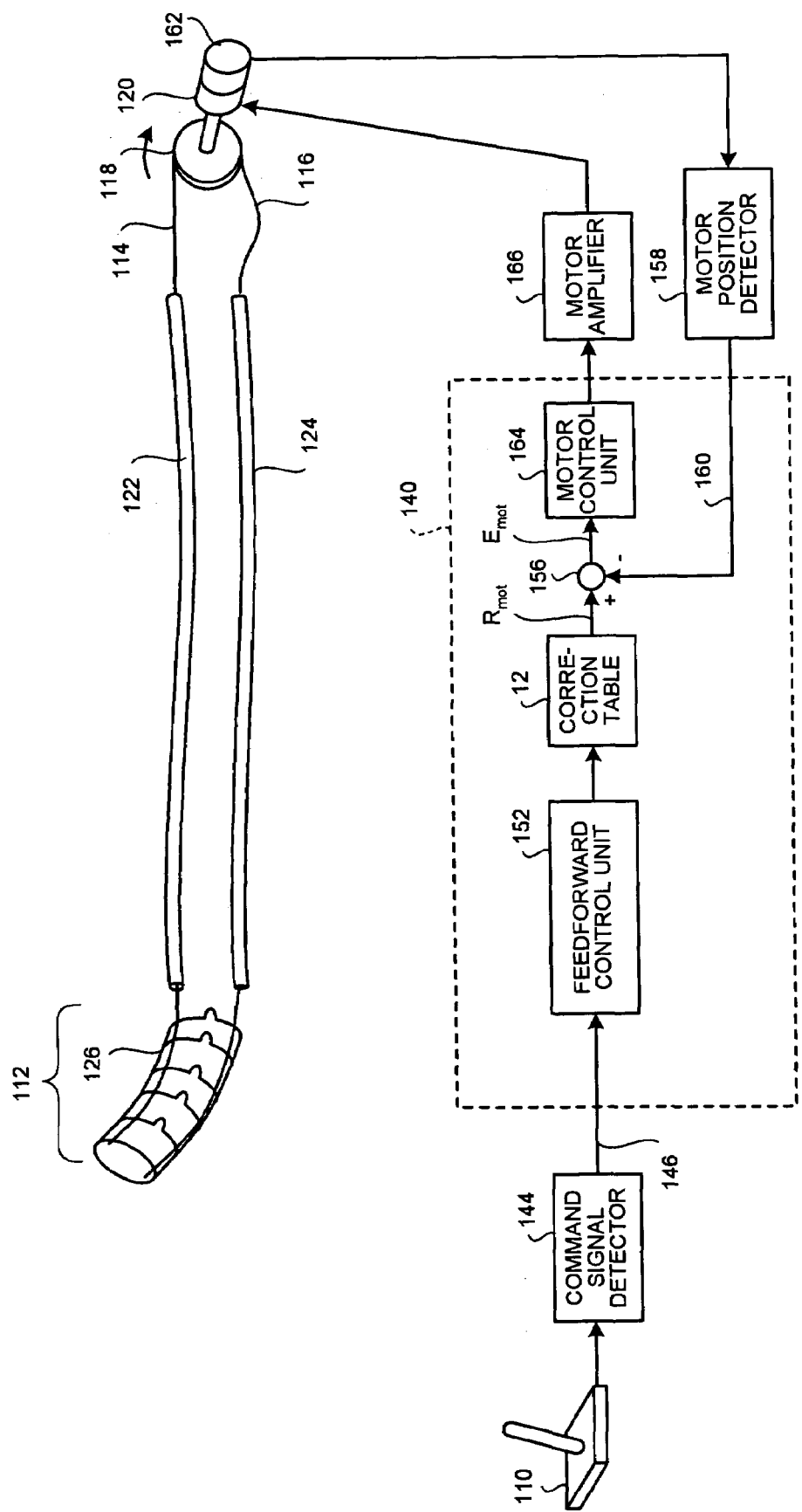
FIG. 28 is a schematic diagram of a motorized endoscope according to a first modification of the fourteenth embodiment of the present invention.
Figure 29:
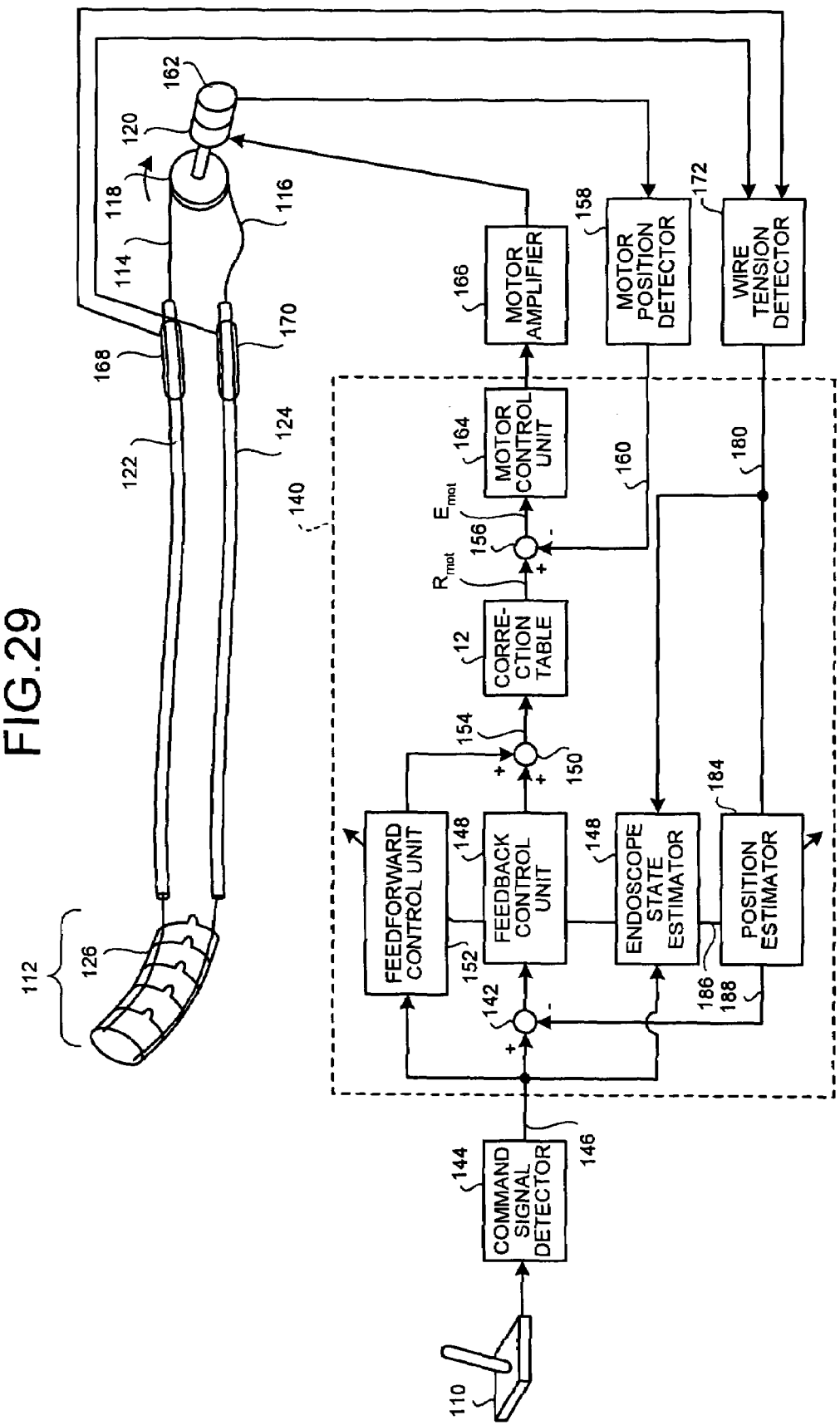
FIG. 29 is a schematic diagram of a motorized endoscope according to a second modification of the fourteenth embodiment.

Similarly, in a motorized endoscope illustrated in FIG. 28, the control device 11 of the first embodiment illustrated in FIG. 1 is applied to the motorized endoscope of the ninth embodiment illustrated in FIG. 16. In a motorized endoscope illustrated in FIG. 29, the control device 11 of the first embodiment illustrated in FIG. 1 is applied to the motorized endoscope of the tenth embodiment illustrated in FIG. 18.

Figure 6:
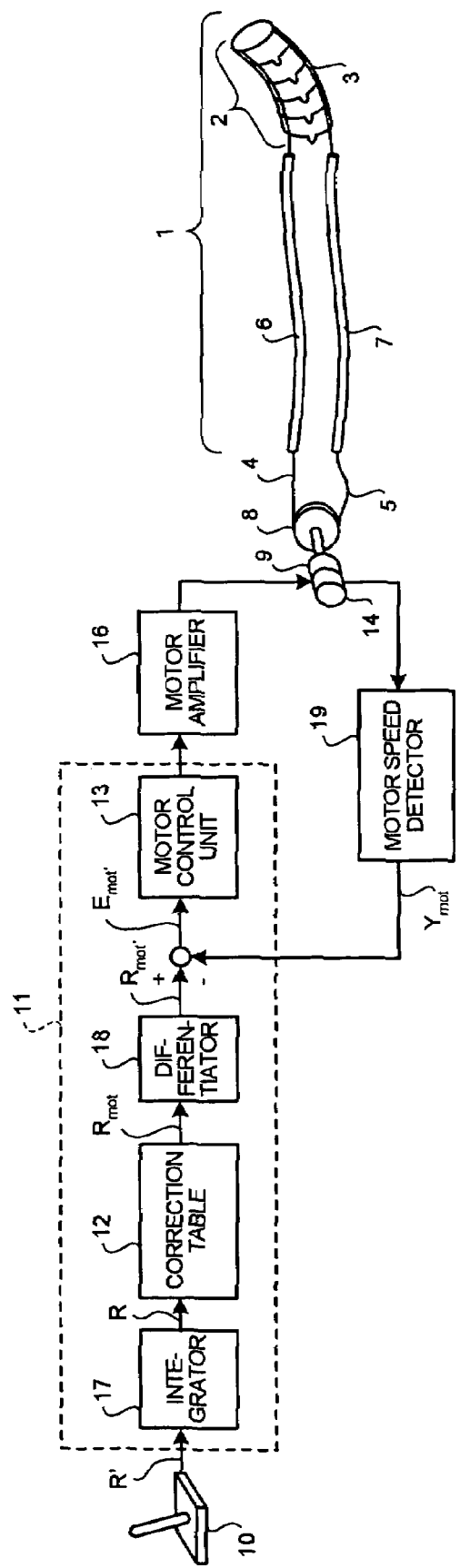
FIG. 6 is a schematic diagram of a motorized endoscope according to a second embodiment of the present invention.
Figure 30:
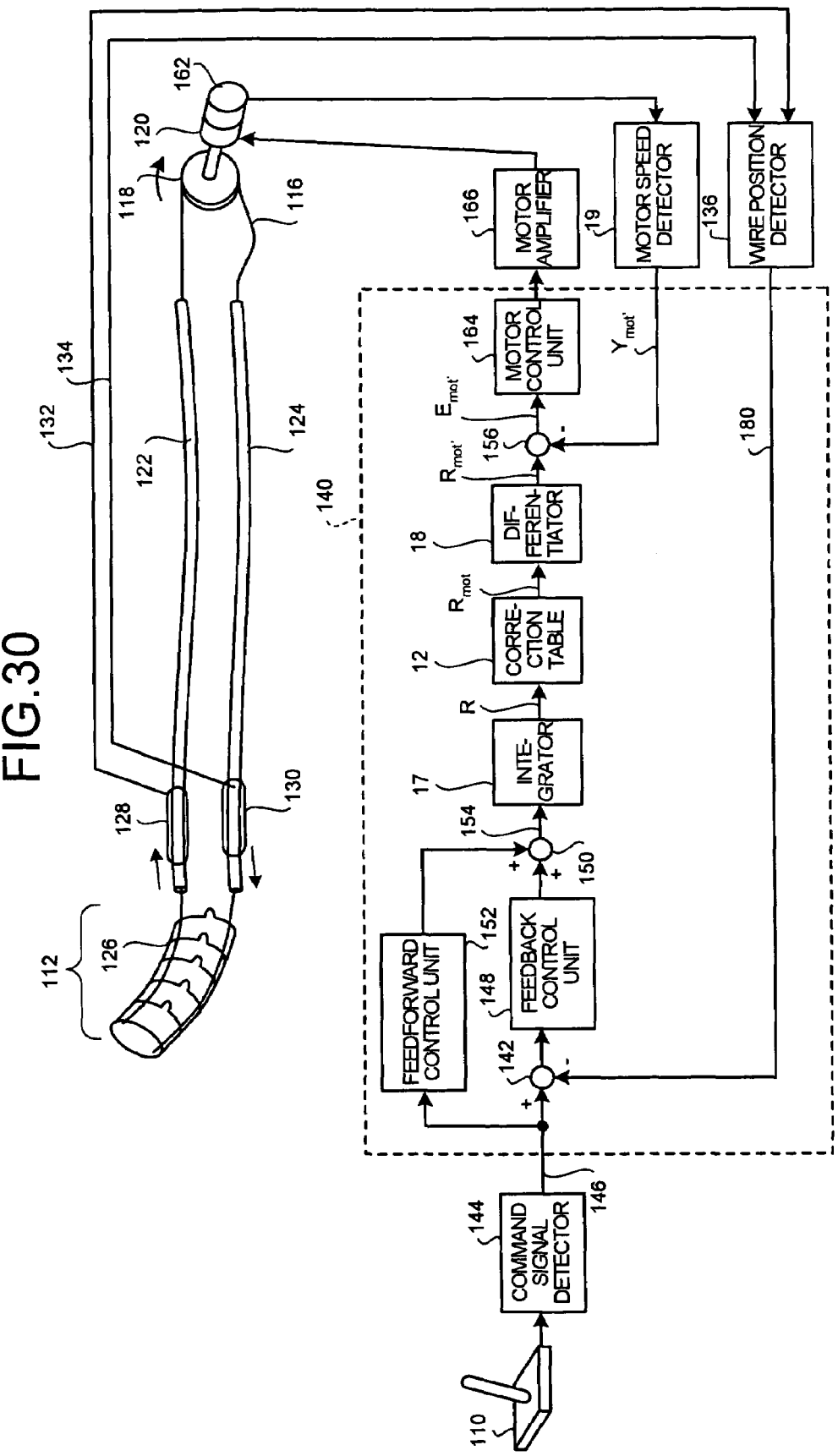
FIG. 30 is a schematic diagram of a motorized endoscope according to a third modification of the fourteenth embodiment.
Figure 31:
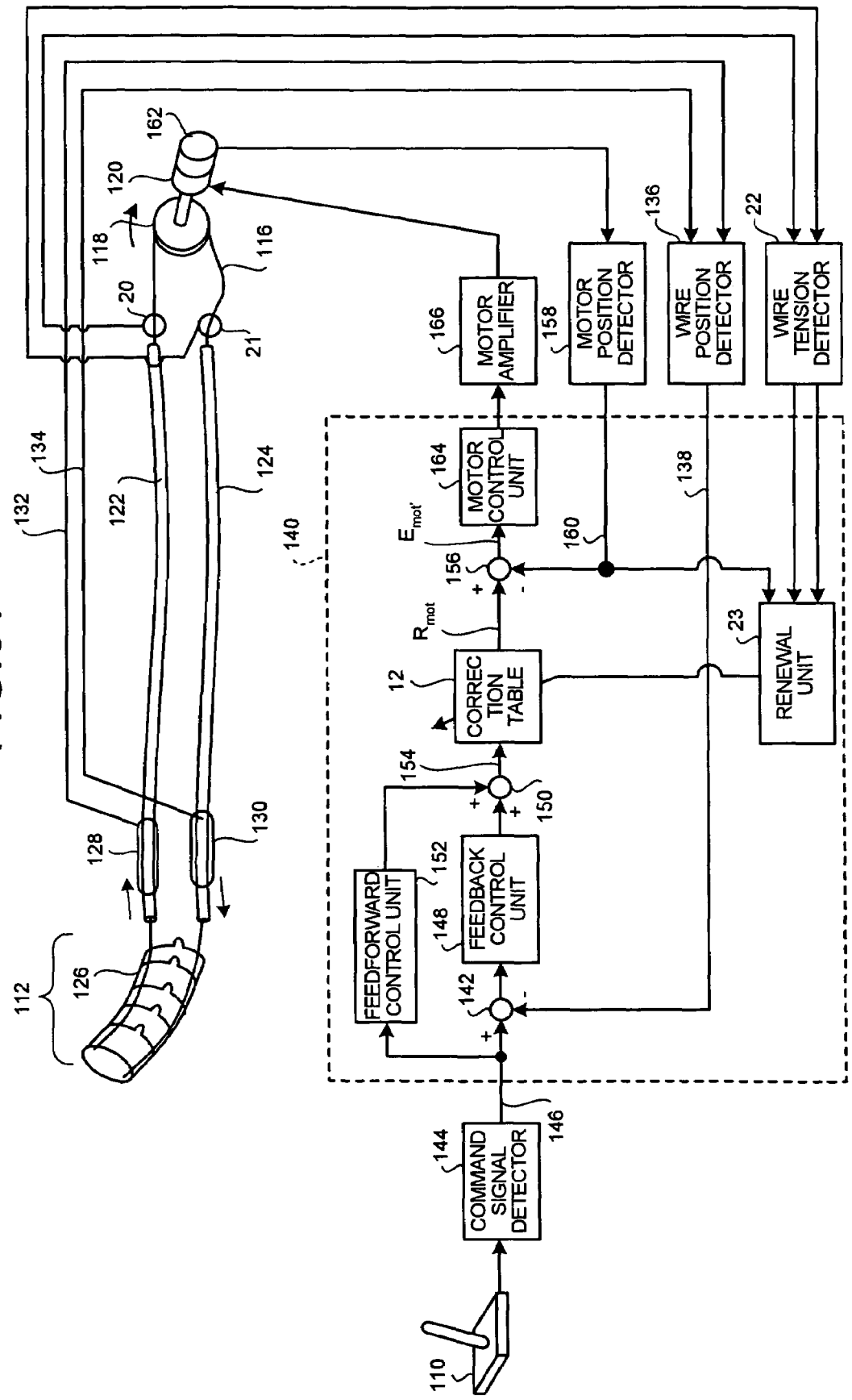
FIG. 31 is a schematic diagram of a motorized endoscope according to a fourth modification of the fourteenth embodiment.
Figure 32:
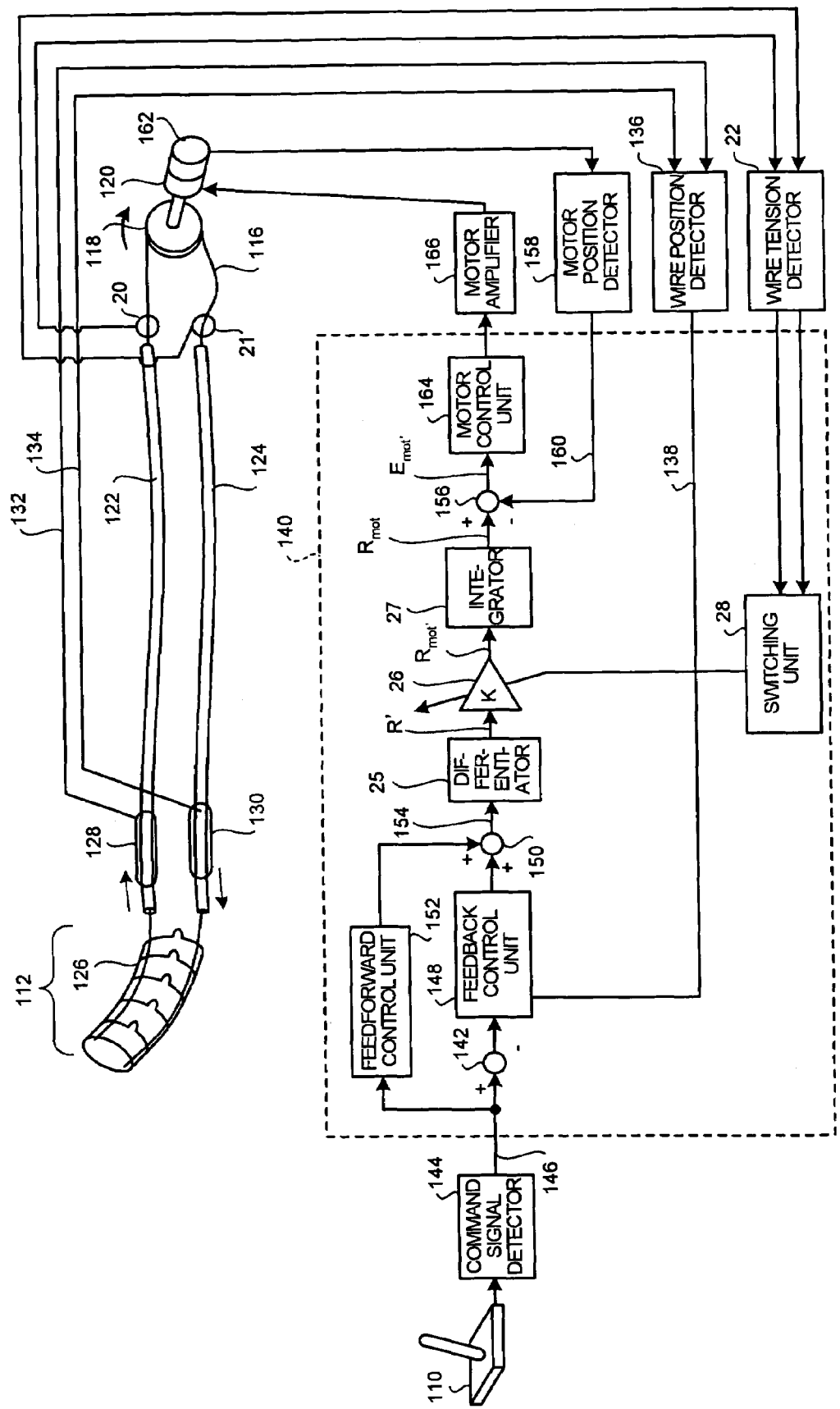
FIG. 32 is a schematic diagram of a motorized endoscope according to a fifth modification of the fourteenth embodiment.

In a motorized endoscope illustrated in FIG. 30, the control device 11 of the second embodiment illustrated in FIG. 6 is applied to the motorized endoscope of the ninth embodiment illustrated in FIG. 16. In a motorized endoscope illustrated in FIG. 31, the control device 11 of the third embodiment illustrated in FIG. 7 is applied to the motorized endoscope of the ninth embodiment illustrated in FIG. 16. In a motorized endoscope illustrated in FIG. 31, the control device 11 of the fifth embodiment illustrated in FIG. 10 is applied to the motorized endoscope of the ninth embodiment illustrated in FIG. 16.

By applying the control device 11 illustrated in the first embodiment to the seventh embodiment to the eighth embodiment to the thirteenth embodiment, the bend position to be operated can instantaneously follow the operation command value, and the operability can be enhanced, and even if slack is generated in both retrieving units at the neutral reference position, the slack can be controlled at the neutral reference position, and it is possible to swiftly and precisely position the towed mechanism.

The embodiments having characteristics have been described to completely and clearly disclose the present invention. However, the accompanying claims should not be limited to the embodiments, and the claims crystallize all of modifications and alternative structures that can be made by a person skilled in the art with a range of basic matters disclosed in this specification.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. Controller for controlling a driving unit for effecting a movement of an actuator mechanism through a hauling unit including a wire wound around the driving unit, wherein both ends of the wire are connected to the actuator mechanism, the controller comprising:
   a control portion for generating and outputting a driving unit control signal for controlling the driving unit based at least upon one of a first control input signal and a second control input signal; and
   an input correction portion for converting a externally-supplied target value into a first correction value by a linear converting operation, wherein a first characteristic curve defined by the first correction value is defined by a first predetermined slope if the received target value is outside a predetermined range within which is indicative of a state wherein both ends of the wire connected to the actuator mechanism are loose, wherein the input correction portion converts the received target value into a second correction value by a proportional converting operation, wherein a second characteristic curve defined by the second correction value is defined by a second predetermined slope that is greater than the first determined slope if the received target value is within the predetermined range, and wherein the first correction value and the second correction value are supplied by the control portion as the first control input signal and the second control input signal, by which the control portion generates and outputs the driving unit control signal to drive the driving unit such that the target value is outside the predetermined range.

2. The apparatus according to claim 1, wherein the input correction portion outputs the first correction value and the second correction value based on the target value, wherein the target value is either of an amount of bending and an amount of rotating of the subject.

3. The controller according to claim 1, wherein the input correction portion determines first correction value and the second correction value by compensating the target value based on a predetermined parameter.

4. The controller according to claim 3, wherein the predetermined parameter is set manually in accordance with degree of extension of the hauling unit.

5. The controller according to claim 1, further comprising:
a notch filter through which the control signal passes to gradually change a differential value of the control signal with respect to the target value near a lower limit and an upper limit of the predetermined range.

6. The controller according to claim 1, further comprising:
a low pass filter through which the control signal passes to gradually change a differential value of the first control input signal with respect to the target value near a lower limit and an upper limit of the predetermined range.

7. The controller according to claim 1, wherein the driving unit is a motor.

8. The controller as set forth in claim 1, wherein the control portion comprises a feedback control portion that generates the driving unit control signal in response to the first and second control input signals, and in response to a rotation position signal indicative of a rotation position of a rotation axis of a motor comprising the driving unit.

9. The controller as set forth in claim 1, wherein the second predetermined slope for the second characteristic curve is defined by a constant "α," wherein α is a real number greater than one, and wherein the first predetermined slope for the first characteristic curve is defined by a constant "α−1."

10. A motorized endoscope, comprising:
a distal end bending section constructed with bending capability;
a motor for effecting a movement of the distal bending section in a first direction, the motor including an actuator;
a hauling unit, the hauling unit comprising:
a pulley fixed to a rotation axis of the motor, wherein a wire comprising a first and a second end is wrapped around the pulley, and wherein the first and second ends are connected to the actuator;
two wire sheaths arranged for protecting separate wire portions that are positioned between the motor and the distal bending section;
an operating unit constructed to operate to generate and output a first target value in response to a user input; and
a controller for controlling motor rotation, the controller comprising:
a first motor control portion that generates and outputs a first motor control signal based at least in part on a control input signal;
an input correction portion for converting the first target value into a first correction value by a linear converting operation, wherein a first characteristic curve defined by the first correction value is defined by a first predetermined slope if the received target value is outside a predetermined range within which is indicative of a state wherein both ends of the wire connected to the actuator mechanism are loose, wherein the input correction portion converts the received target value into a second correction value by a proportional converting operation, wherein a second characteristic curve defined by the second correction value is defined by a second predetermined slope that is greater than the first determined slope if the received target value is within the predetermined range, and wherein the first correction value and the second correction value are supplied by the control portion as the control input signal by which the control portion generates and outputs the driving unit control signal to drive the driving unit such that the target value is outside the predetermined range.

11. The controller according to claim 10, wherein the operating unit is a joystick.

12. The endoscope as set forth in claim 10, wherein the control portion comprises a feedback control portion that generates the driving unit control signal in response to the control input signal, and in response to a rotation position signal indicative of a rotation position of a rotation axis of the motor.

13. The endoscope as set forth in claim 10, further comprising:
a second motor and a second hauling unit for effecting a movement of the distal bending section in a second direction that is substantially orthogonal to movement in the first direction, wherein said operating unit comprises a portion for outputting a second target value corresponding to the second direction; and
wherein the controller further comprises a second input correction portion and a second motor control portion, which second input correction portion and second motor control portion to process the second target value.

* * * * *